US010696622B2

(12) United States Patent
Dumoleijn et al.

(10) Patent No.: US 10,696,622 B2
(45) Date of Patent: Jun. 30, 2020

(54) SYNTHESIS OF N-VINYL CARBOXYLIC ACID AMIDES

(71) Applicant: Taminco BVBA, Ghent (BE)

(72) Inventors: Kim Dumoleijn, Eede (NL); Kristof Moonen, Hamme (BE); Alexis Henricot, Ghent (BE); Cai Xing Simon Han, Shanghai (CN)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 15/669,989

(22) Filed: Aug. 7, 2017

(65) Prior Publication Data

US 2018/0057445 A1    Mar. 1, 2018

Related U.S. Application Data

(60) Provisional application No. 62/380,774, filed on Aug. 29, 2016.

(51) Int. Cl.
*C07C 231/12* (2006.01)
*C07C 233/17* (2006.01)
(Continued)

(52) U.S. Cl.
CPC .......... *C07C 231/12* (2013.01); *C07C 231/08* (2013.01); *C07C 233/03* (2013.01); *C07C 233/17* (2013.01); *C07C 233/18* (2013.01)

(58) Field of Classification Search
None
See application file for complete search history.

(56) References Cited

U.S. PATENT DOCUMENTS 3,526,620 A * 9/1970 Bestian .............. C07D 207/267
540/451
4,567,300 A * 1/1986 Murao .................. C07C 233/18
564/215

(Continued)

FOREIGN PATENT DOCUMENTS

DE   21 13 338 A1   9/1972
EP   0 184 074 A1   6/1986
(Continued)

OTHER PUBLICATIONS

Sauer ("Tubular Plug Flow Reactors" Ullmann's Encyclopedia of Industrial Chemistry, p. 1-23, first published on Oct. 9, 2013, https://doi.org/10.1002/14356007.b04_181.pub2) (Year: 2013).*
N-Methylformamide ("N-Methylformamide" Sigma Aldrich properties sheet, downloaded from https://www.sigmaaldrich.com/catalog/product/aldrich/473936?lang=en&region=US on Jul. 9, 2018, p. 1-3) (Year: 2018).*

(Continued)

*Primary Examiner* — Amy C Bonaparte
(74) *Attorney, Agent, or Firm* — Dennis V. Carmen

(57) ABSTRACT

Processes and systems for producing N-vinyl carboxylic acid amides are provided herein. According to some aspects of the present invention, a process for producing an N-vinyl carboxylic acid amide is described that eliminates interim solids handling steps during formation of the intermediate compounds, thereby increasing efficiency and reducing cost. The processes and system described herein may be used for the synthesis of N-vinylformamide and its intermediates, including 1-hydroxyethylformamide and 1-alkoxyethylformamide, or for the synthesis of N-methyl,N-vinylformamide and its intermediates, including N-methyl,1-hydroxyethylformamide and N-methyl,1alkoxyethylformamide.

15 Claims, 4 Drawing Sheets

(51) Int. Cl.
    *C07C 233/03*    (2006.01)
    *C07C 231/08*    (2006.01)
    *C07C 233/18*    (2006.01)

(56) References Cited

U.S. PATENT DOCUMENTS

| | | |
|---|---|---|
| 4,578,515 A | 3/1986 | Dawson et al. |
| 5,527,963 A | 6/1996 | Sato et al. |
| 2011/0294974 A1* | 12/2011 | Ohta .................. C07C 231/12 |
| | | 526/303.1 |

FOREIGN PATENT DOCUMENTS

| | | |
|---|---|---|
| EP | 0 251 118 A2 | 1/1988 |
| EP | 2 386 538 A1 | 11/2011 |
| WO | WO 2010/079774 A1 | 7/2010 |

OTHER PUBLICATIONS

N-Methyl-N-vinylformamide ("N-Methyl-N-vinylformamide" Alfa Chemistry properties sheet, downloaded from http://www.alfa-chemistry.com/cas_2867-48-3.htm on Jul. 9, 2018, p. 1-2). (Year: 2018).*

Definition for "solution" (1992) in C.G. Morris (ed.), Academic Press Dictionary of Science and Technology (4th ed) Oxford, UK, Elsevier Science and Technology, retrieved from https://search.credoreference.com/content/entry/apdst/solution/0?institutionId=743, downloaded on Feb. 14, 2019 (Year: 2019).*

Notification of Transmittal of the International Search Report and the Written Opinion of the International Searching Authority dated Oct. 20, 2017 for International Application No. PCT/EP2017/070584.

* cited by examiner

SYNTHESIS OF N-VINYL CARBOXYLIC ACID AMIDES

CROSS REFERENCE TO RELATED APPLICATIONS

This application claims the benefit of Provisional Application 62/380,774 filed on Aug. 29, 2016 under 35 USC § 119(e)(1), the entire content of which is incorporated herein by reference.

BACKGROUND

1. Field of the Invention

The present invention relates generally to carboxylic acid amides. In particular, this invention relates to methods of synthesizing N-vinylformamide and N-methyl,N-vinylformamide and their intermediates, as well as compositions including one or more of the same.

2. Description of Related Art

N-vinylformamide is the simplest member of the enamide group and is a key compound used in the synthesis of cationic polymers with reactive primary amino groups. Such polymers are desirable both for their primary amine functionality and water solubility, and their low toxicity has made them useful in a wide variety of applications in many technical fields. For example, polyvinylamines derived from N-vinylformamide have been successfully employed as flocculants in water treatment, as well as additives for the paper making, chemical and petroleum refining industries. These polymers have also been useful as carriers for non-absorbable food dyes, catalysts, drugs, and as dye acceptors for synthetic fibers. Additionally, such cationic polyvinylamine polymers may also be used in various ink, adhesive, and pigment formulations, as well as in other formulations for commercial and industrial paints and coatings, as well as in several types of personal care, biomedical, and consumer products. Similarly, N-methyl,N-vinylformamide is a key compound in the synthesis of cationic polymers with reactive secondary amino groups and has certain applications in the paper industry and in the petroleum refining industries.

Several processes exist for synthesizing N-vinylformamide and N-methyl,N-vinylformamide. Industrially, the three most viable reaction pathways for N-vinylformamide described in literature include the general steps of reacting acetaldehyde and formamide in the presence of another compound, such as hydrogen cyanide or an alcohol, to form at least one intermediate, then thermally and/or chemically decomposing the intermediate to form N-vinylformamide. More specifically, EP0184074 describes the first of the most common industrial processes which includes reacting acetaldehyde and hydrogen cyanide with formamide to form 1-cyanoethylformamide, which is then decomposed to form N-vinylformamide. The second of the most common process, described in U.S. Pat. Nos. 4,567,300 and 5,527,963, involves reacting acetaldehyde and formamide to form an intermediary 1-hydroxyethylformamide, which is then reacted with methanol to form 1-methoxyethylformamide. Subsequent thermal and/or chemical decomposition of the 1-methoxyethylformamide eliminates methanol, forming N-vinylformamide. U.S. Pat. No. 4,578,515 describes a third process which involves reacting a large excess of formamide with acetaldehyde to form N-(alpha-N'-formamidoethyl) formamide, which is subsequently decomposed to form formamide and the desired N-vinylformamide. There is only one synthesis route described in literature for the synthesis of N-methyl,N-vinylformamide. WO 2010079774 describes the synthesis of N-methyl,N-vinylformamide that includes the reaction of acetaldehyde with N-methylformamide to form an intermediary N-methyl,1-hydroxyethylformamide which is then reacted with methanol to form N-methyl,1-methoxyethylformamide. Subsequent thermal and/or chemical decomposition of this compound splits off methanol, forming N-methyl,N-vinylformamide.

There are however several drawbacks associated with the above synthesis methods. Hydrogen cyanide is a toxic gaseous component which is difficult to handle and which can't be stored. Therefore, extreme safety measurements have to be taken to be able to use this route industrially. Additionally, the industrial synthesis of N-vinylformamide and N-methyl,N-vinylformamide via 1-methoxyethylformamide and N-methyl,1-methoxyethylformamide, respectively, needs an intermediary precipitation step for the 1-hydroxyethylformamide and N-methyl,1-hydroxyethylformamide, respectively. These components are insoluble in the applied reaction medium so that the intermediate compound precipitates out of the solution when formed. Industrially, this is addressed by including a solids handling step in the process for filtering, washing, and redissolving the solid intermediate before reintroducing the new solution into a subsequent reaction zone for further processing into N-vinylformamide or N-methyl, N-vinylformamide as described above. Unfortunately, implementation of such solids handling steps tend to be expensive, both in terms of cost and processing time, and, as a result, are undesirable in a commercial-scale production facility. The third mentioned process, the synthesis of N-vinylformamide via N-(alpha-N'-formamidoethyl)formamide has the drawback that deactivation of the used catalyst occurs very rapidly and it is difficult to maintain a high purity and yield of the intermediate product.

Therefore, a need exists for a more efficient process for producing N-vinylformamide and N-methyl,N-vinylformamide that minimizes or prevents precipitation of intermediate compounds from the reaction solution and which uses less toxic components. Ideally, such a process would be easily implemented on a commercial scale and produces high product yields in a continuous way at a minimal cost.

SUMMARY

Embodiments of the present invention concerns a process for the synthesis of the intermediary 1-hydroxyethylformamide or N-methyl,1-hydroxyethylformamide which is then used in consecutive steps to produce respectively the N-vinylformamide or N-methyl,N-vinylformamide. The process can include the step of reacting formamide or N-methylformamide and acetaldehyde in the presence of a solvent wherein the molar ratio of formamide or N-methylformamide to acetaldehyde added to the first reaction zone is at least 1.1:1. The process can also include the step of reacting at least a portion of the formamide or N-methylformamide with at least a portion of acetaldehyde in the presence of a basic catalyst to thereby form a reaction mixture comprising 1-hydroxyethylformamide or N-methyl,1-hydroxyethylformamide in the absence of a solvent wherein the molar ratio of formamide or N-methylformamide to acetaldehyde added to the first reaction zone is at least 1.5:1. At least a portion of formamide or N-methylformamide can react with at least a portion of acetaldehyde in the presence of a basic catalyst to thereby form a reaction mixture comprising 1-hydroxyethylformamide or N-methyl, 1-hydroxyethylformamide in respectively an excess formamide or N-methylformamide or in the presence of a solvent. When the first reaction mixture includes a solvent other than formamide or N-methylformamide, the 1-hydroxyethylformamide or N-methyl,1-hydroxyethylformamide has a solubility of at least 20 weight percent in the solvent. Additionally, at least 90 weight percent of the 1-hydroxyethylformamide or N-methyl,1-hydroxyethylformamide formed during the reaction step can be maintained in solution in the first reaction mixture.

Another embodiment of the present invention concerns a process for making N-vinylformamide or N-methyl,N-vinylformamide that includes introducing formamide or N-methylformamide and acetaldehyde into a first reaction zone, as described above, and then combining the reaction mixture of 1-hydroxyethylformamide or N-methyl,1-hydroxyethylformamide, with an additional solvent or with an excess of formamide or N-methylformamide, with at least one alcohol and an acid catalyst, and alkoxylating at least a portion of the 1-hydroxyethylformamide or N-methyl,1-hydroxyethylformamide to thereby form another reaction mixture comprising 1-alkoxyethylformamide or N-methyl, 1-alkoxyethylformamide. One or more intermediary separation steps may also be performed in order to provide a stream including 1-alkoxyethylformamide or N-methy,1-alkoxyethylformamide, optionally including formamide or N-methylformamide.

Yet another embodiment of the present invention concerns introducing a feed stream comprising the 1-alkoxyethylformamide or N-methyl,1-alkoxyethylformamide and at least 1 weight percent formamide, based on the total weight of the feed stream, into a pyrolysis zone and pyrolyzing at least a portion of the 1-alkoxyethylformamide or N-methyl,1-alkoxyethylformamide to thereby form N-vinylformamide or N-methyl,N-vinylformamide and an alcohol, and withdrawing a crude product stream from the pyrolysis zone. The crude product stream comprises the N-vinylformamide or N-methyl,N-vinylformamide and at least 1 weight percent formamide or N-methylformamide, based on the total weight of the crude product stream. Thereafter, the N-vinylformamide or N-methyl,N-vinylformamide can be recovered from the crude product stream.

A further embodiment of the present invention concerns a composition comprising at least 1 weight percent of formamide or N-methylformamide and at least 35 weight percent of 1-alkoxyethylformamide or N-methyl,1-alkoxyethylformamide.

BRIEF DESCRIPTION OF THE DRAWINGS

Various embodiments of the present invention are described in detail below with reference to the attached drawing Figures, wherein.

DETAILED DESCRIPTION

Various embodiments of the present invention relate to methods and systems for making N-vinylformamide and N-methyl,N-vinylformamide, as well as compositions including the same. More specifically, in some embodiments, the present invention relates to methods of reacting an acetaldehyde and formamide or N-methylformamide to form a 1-hydroxyethylformamide or N-methyl,1-hydroxyethylformamide, respectively, and reacting the 1-hydroxyethylformamide or N-methyl,1-hydroxyethylformamide, with at least one alcohol to form 1-alkoxyethylformamide or N-methyl,1-alkoxyethylformamide, respectively. The resulting component can subsequently be thermally and/or chemically decomposed to provide an alcohol and respectively the N-vinylformamide or N-methyl,N-vinylformamide. Various separation steps may also be employed as discussed in further detail below. According to some embodiments, the method described herein minimizes or prevents the precipitation of one or more of the intermediate products, such as 1-hydroxyethylformamide or N-methyl,1-hydroxyethylformamide and 1-alkoxyethylformamide or N-methyl,1-alkoxyethylformamide, in order to eliminate the need for a solids handling step. As a result, the process is more efficient, and the N-vinyl carboxylic acid amide, such as N-vinylformamide or N-methyl,N-vinylformamide, can be produced in a continuous manner so as to minimize reaction time and maximize yield.

Figure 1:
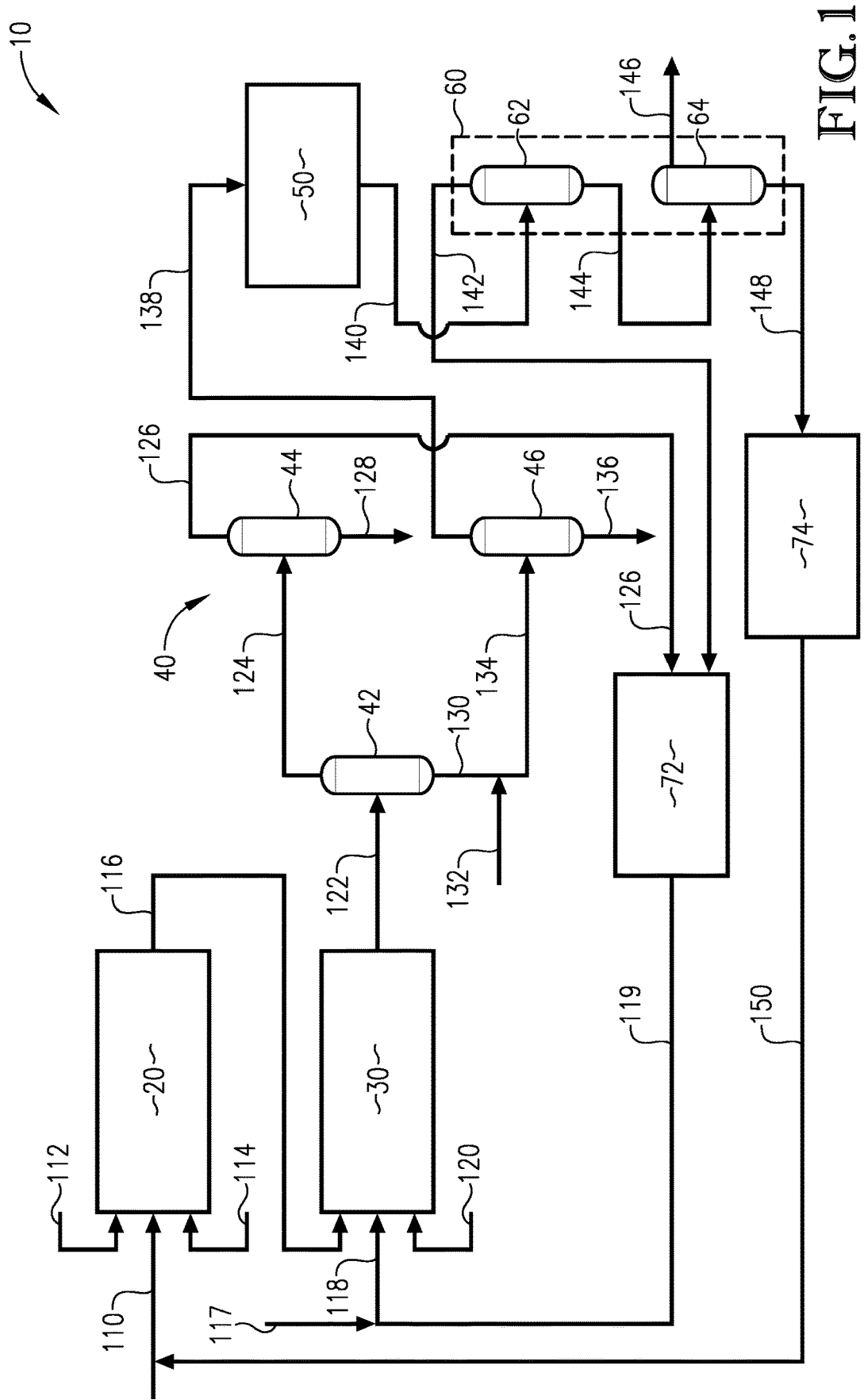
FIG. 1 is a schematic overview of a facility for producing an N-vinyl carboxylic acid amide according to various embodiments of the present invention, particularly illustrating the main steps of the synthesis process.

Referring initially to FIG. 1, a schematic diagram is provided outlining the major processing zones of a facility 10 for producing N-vinylformamide or N-methyl,N-vinylformamide, configured according to various embodiments of the present invention. As shown in FIG. 1, facility 10 includes a first reaction zone 20, a second reaction zone 30, an intermediate separation zone 40, a pyrolysis zone 50, and a final separation zone 60. Reactants, which typically include at least one amide, such as formamide or N-methylformamide, and acetaldehyde are introduced into first reaction zone 20, along with a basic catalyst, and are reacted to form a 1-hydroxyethylcarboxamide, such as 1-hydroxyethylformamide or N-methyl,-1-hydroxyethylformamide. The stream withdrawn from first reaction zone 20 can then be combined with at least one alcohol and another catalyst prior to being introduced into second reaction zone 30, wherein the 1-hydroxyethylcarboxamide is alkoxylated to form a 1-alkoxyethylcarboxamide, such as a 1-alkoxyethylformamide or N-methyl,1-alkoxyethylformamide. In other embodiments, the 1-hydroxyethylcarboxamide may be further reacted with other components, including for example, formamide (or other carboxylic acid amide such as N-methylformamide) to form a N,N'-ethylidenebiscarboxamide, hydrogencyanide to form a 1-cyanoethylcarboxamide, or an acid to form a 1-carboxamido-ethylcarboxylate.

When the 1-hydroxyethylcarboxamide is reacted to form a 1-alkoxyethylcarboxamide, the 1-alkoxyethylcarboxamide withdrawn from second reaction zone 30 can be passed through intermediate separation zone 40 to remove various impurities, including residual catalysts, unreacted starting materials, and various byproducts, from the 1-alkoxyethylcarboxamide stream before the resulting purified 1-alkoxyethylcarboxamide is introduced into pyrolysis zone 50. In pyrolysis zone 50, the 1-alkoxyethylcarboxamide may be chemically and/or thermally decomposed to provide the desired N-vinyl carboxylic acid amide and an alcohol byproduct. As shown in FIG. 1, passage of the crude product stream through final separation zone 60 provides purified product and recycle streams, which can be routed to one or more locations within or outside of facility 10 for further processing, storage, and/or reuse.

In some embodiments, facility 10 can be used to produce N-vinylformamide by reacting formamide and acetaldehyde in first reaction zone 20 to produce 1-hydroxyethylformamide, alkoxylating at least a portion of the 1-hydroxyethylformamide in second reaction zone 30 to form 1-alkoxyethylformamide, and pyrolyzing at least a portion of the 1-alkoxyethylformamide in pyrolysis zone 50 in order to provide a crude N-vinylformamide, which can subsequently be purified in final separation zone 60, as shown in FIG. 1. Although generally described herein with respect to the formation of N-vinylformamide, it should be understood that processes and systems of the present invention may also be utilized in the production of other types of amide monomers and, in particular, other types of N-vinyl carboxylic acid amides such as N-methyl,N-vinylformamide. Further, although described herein with respect to intermediate compounds including 1-hydroxyethylformamide and 1-alkoxyethylformamide, it should be understood other 1-hydroxyethylcarboxamide and 1-alkoxyethylcarboxamide intermediates may also be present, in addition or in the alternative, depending on the type of N-vinyl carboxylic acid amide being synthesized within facility 10. For example, when facility 10 is used to produce N-methyl,N-vinylformamide, the intermediate compounds N-methyl,1-hydroxylethylformamide and N-methyl,1-alkoxyethylformamide will be present in various process streams described in detail below as including 1-hydroxyethylformamide and 1-alkoxyethylformamide.

Referring again to FIG. 1, two or more reagents, such as, for example, formamide and acetaldehyde, may be introduced into at least one reaction vessel (not shown) in first reaction zone 20 via lines 110 and 112, respectively. Additionally, at least one basic catalyst may also be added to first reaction zone 20 via line 114 as in FIG. 1. Although shown in FIG. 1 as being introduced via separate lines 110, 112, and 114, in some embodiments, one or more of the starting materials may be combined with one or more of the other starting materials prior to entering first reaction zone 20, while, in other embodiments, one or more starting materials may be separately added. For example, the formamide (or other carboxylic acid amide such as N-methylformamide) and catalyst in respective lines 110 and 114 may be combined into a single stream prior to entering first reaction zone 20 (not shown), and the acetaldehyde may be added via line 112. Alternatively, each of the starting components may be added separately, and may combine upon introduction into the reaction vessel within first reaction zone 20. When added separately, the components may be added in any suitable order, or two or more of the components may be added simultaneously. The order and method of adding each of the starting materials may depend on the type and number of reaction vessels employed, as well as the specific synthesis reaction being performed.

As discussed above, the reagents introduced into first reaction zone 20 via lines 110 and 112 may include formamide (or other carboxylic acid amide such as N-methylformamide) and acetaldehyde, respectively. Although the amounts of formamide and acetaldehyde may be present in amounts close to stoichiometric, one of the materials may also be present in a stoichiometric excess. For example, in some embodiments, an excess of formamide or other carboxylic acid amide may be employed such that the ratio of formamide to acetaldehyde introduced into first reaction zone 20 may be at least about 1.1:1, at least about 1.2:1, at least about 1.3:1, at least about 1.4:1, at least about 1.5:1, at least about 1.6:1, at least about 1.7:1, at least about 1.75:1, at least about 1.8:1, at least about 1.9:1, at least about 2:1, at least about 2.1:1, or at least about 2.2:1 and/or not more than about 5:1, not more than about 4:1, not more than about 3:1, not more than about 2.5:1, or not more than about 2.25:1, on a molar basis.

The molar ratio of formamide (or other carboxylic acid amide, such as N-methylformamide) to acetaldehyde can be in the range of from about 1.1:1 to about 5:1, about 1.2:1 to about 5:1, about 1.3:1 to about 5:1, about 1.4:1 to about 5:1, about 1.5:1 to about 5:1, about 1.6:1 to about 5:1, about 1.7:1 to about 5:1, about 1.75:1 to about 5:1, about 1.8:1 to about 5:1, about 1.9:1 to about 5:1, about 2:1 to about 5:1, about 2.1:1 to about 5:1, about 2.2:1 to about 5:1, about 1.1:1 to about 4:1, about 1.2:1 to about 4:1, about 1.3:1 to about 4:1, about 1.4:1 to about 4:1, about 1.5:1 to about 4:1, about 1.6:1 to about 4:1, about 1.7:1 to about 4:1, about 1.75:1 to about 4:1, about 1.8:1 to about 4:1, about 1.9:1 to about 4:1, about 2:1 to about 4:1, about 2.1:1 to about 4:1, about 2.2:1 to about 4:1, about 1.1:1 to about 3:1, about 1.2:1 to about 3:1, about 1.3:1 to about 3:1, about 1.4:1 to about 3:1, about 1.5:1 to about 3:1, about 1.6:1 to about 3:1, about 1.7:1 to about 3:1, about 1.75:1 to about 3:1, about 1.8:1 to about 3:1, about 1.9:1 to about 3:1, about 2:1 to about 3:1, about 2.1:1 to about 3:1, about 2.2:1 to about 3:1, about 1.1:1 to about 2.5:1, about 1.2:1 to about 2.5:1, about 1.3:1 to about 2.5:1, about 1.4:1 to about 2.5:1, about 1.5:1 to about 2.5:1, about 1.6:1 to about 2.5:1, about 1.7:1 to about 2.5:1, about 1.75:1 to about 2.5:1, about 1.8:1 to about 2.5:1, about 1.9:1 to about 2.5:1, about 2:1 to about 2.5:1, about 2.1:1 to about 2.5:1, about 2.2:1 to about 2.5:1, about 1.1:1 to about 2.25:1, about 1.2:1 to about 2.25:1, about 1.3:1 to about 2.25:1, about 1.4:1 to about 2.25:1, about 1.5:1 to about 2.25:1, about 1.6:1 to about 2.25:1, about 1.7:1 to about 2.25:1, about 1.75:1 to about 2.25:1, about 1.8:1 to about 2.25:1, about 1.9:1 to about 2.25:1, about 2:1 to about 2.25:1, about 2.1:1 to about 2.25:1, or about 2.2:1 to about 2.25:1. Alternatively, in some embodiments, an excess of acetaldehyde may be employed such that the ratio of acetaldehyde to formamide may fall within one or more of the above ranges.

The amount of catalyst added to first reaction zone 20 via line 114 may be an amount sufficient to catalyze the reaction between formamide (or other carboxylic acid amide such as N-methylformamide) and acetaldehyde to a desirable yield. In some embodiments, the amount of catalyst introduced into first reaction zone 20 via line 114 can be at least about 0.2, at least about 0.3, at least about 0.4, at least about 0.5, at least about 0.6, at least about 0.7, at least about 0.75, at least about 0.8, at least about 0.85, at least about 0.9, at least about 0.95, at least about 1.0, at least about 1.05, at least about 1.1, at least about 1.15, at least about 1.2, at least about 1.25, at least about 1.3, at least about 1.4, or at least about 1.5 weight percent and/or not more than about 10, not more than about 5, not more than about 2.5, not more than about 2.25, not more than about 2.0, not more than about 1.75, or not more than about 1.5 weight percent, based on the total weight of the initial reaction mixture.

The catalyst added to first reaction zone 20 via line 114 may be present in an amount in the range of from about 0.2 to about 10 weight percent, about 0.3 to about 10 weight percent, about 0.4 to about 10 weight percent, about 0.5 to about 10 weight percent, about 0.6 to about 10 weight percent, about 0.7 to about 10 weight percent, about 0.75 to about 10 weight percent, about 0.8 to about 10 weight percent, about 0.85 to about 10 weight percent, about 0.9 to about 10 weight percent, about 0.95 to about 10 weight percent, about 1.0 to about 10 weight percent, about 1.05 to about 10 weight percent, about 1.1 to about 10 weight percent, about 1.15 to about 10 weight percent, about 1.2 to about 10 weight percent, about 1.25 to about 10 weight percent, about 1.3 to about 10 weight percent, about 1.4 to about 10 weight percent, about 1.5 to about 10 weight percent, about 0.2 to about 5 weight percent, about 0.3 to about 5 weight percent, about 0.4 to about 5 weight percent, about 0.5 to about 5 weight percent, about 0.6 to about 5 weight percent, about 0.7 to about 5 weight percent, about 0.75 to about 5 weight percent, about 0.8 to about 5 weight percent, about 0.85 to about 5 weight percent, about 0.9 to about 5 weight percent, about 0.95 to about 5 weight percent, about 1.0 to about 5 weight percent, about 1.05 to about 5 weight percent, about 1.1 to about 5 weight percent, about 1.15 to about 5 weight percent, about 1.2 to about 5 weight percent, about 1.25 to about 5 weight percent, about 1.3 to about 5 weight percent, about 1.4 to about 5 weight percent, about 1.5 to about 5 weight percent.

The catalyst added to first reaction zone 20 via line 114 may be present in an amount in the range of from about 0.2 to about 2.5 weight percent, about 0.3 to about 2.5 weight percent, about 0.4 to about 2.5 weight percent, about 0.5 to about 2.5 weight percent, about 0.6 to about 2.5 weight percent, about 0.7 to about 2.5 weight percent, about 0.75 to about 2.5 weight percent, about 0.8 to about 2.5 weight percent, about 0.85 to about 2.5 weight percent, about 0.9 to about 2.5 weight percent, about 0.95 to about 2.5 weight percent, about 1.0 to about 2.5 weight percent, about 1.05 to about 2.5 weight percent, about 1.1 to about 2.5 weight percent, about 1.15 to about 2.5 weight percent, about 1.2 to about 2.5 weight percent, about 1.25 to about 2.5 weight percent, about 1.3 to about 2.5 weight percent, about 1.4 to about 2.5 weight percent, about 1.5 to about 2.5 weight percent, about 0.2 to about 2.25 weight percent, about 0.3 to about 2.25 weight percent, about 0.4 to about 2.25 weight percent, about 0.5 to about 2.25 weight percent, about 0.6 to about 2.25 weight percent, about 0.7 to about 2.25 weight percent, about 0.75 to about 2.25 weight percent, about 0.8 to about 2.25 weight percent, about 0.85 to about 2.25 weight percent, about 0.9 to about 2.25 weight percent, about 0.95 to about 2.25 weight percent, about 1.0 to about 2.25 weight percent, about 1.05 to about 2.25 weight percent, about 1.1 to about 2.25 weight percent, about 1.15 to about 2.25 weight percent, about 1.2 to about 2.25 weight percent, about 1.25 to about 2.25 weight percent, about 1.3 to about 2.25 weight percent, about 1.4 to about 2.25 weight percent, about 1.5 to about 2.25 weight percent, about 0.2 to about 2.0 weight percent, about 0.3 to about 2.0 weight percent, about 0.4 to about 2.0 weight percent, about 0.5 to about 2.0 weight percent, about 0.6 to about 2.0 weight percent, about 0.7 to about 2.0 weight percent, about 0.75 to about 2.0 weight percent, about 0.8 to about 2.0 weight percent, about 0.85 to about 2.0 weight percent, about 0.9 to about 2.0 weight percent, about 0.95 to about 2.0 weight percent, about 1.0 to about 2.0 weight percent, about 1.05 to about 2.0 weight percent, about 1.1 to about 2.0 weight percent, about 1.15 to about 2.0 weight percent, about 1.2 to about 2.0 weight percent, about 1.25 to about 2.0 weight percent, about 1.3 to about 2.0 weight percent, about 1.4 to about 2.0 weight percent, about 1.5 to about 2.0 weight percent, about 0.2 to about 1.75 weight percent, about 0.3 to about 1.75 weight percent, about 0.4 to about 1.75 weight percent, about 0.5 to about 1.75 weight percent, about 0.6 to about 1.75 weight percent, about 0.7 to about 1.75 weight percent, about 0.75 to about 1.75 weight percent, about 0.8 to about 1.75 weight percent, about 0.85 to about 1.75 weight percent, about 0.9 to about 1.75 weight percent, about 0.95 to about 1.75 weight percent, about 1.0 to about 1.75 weight percent, about 1.05 to about 1.75 weight percent, about 1.1 to about 1.75 weight percent, about 1.15 to about 1.75 weight percent, about 1.2 to about 1.75 weight percent, about 1.25 to about 1.75 weight percent, about 1.3 to about 1.75 weight percent, about 1.4 to about 1.75 weight percent, about 1.5 to about 1.75 weight percent, about 0.2 to about 1.5 weight percent, about 0.3 to about 1.5 weight percent, about 0.4 to about 1.5 weight percent, about 0.5 to about 1.5 weight percent, about 0.6 to about 1.5 weight percent, about 0.7 to about 1.5 weight percent, about 0.75 to about 1.5 weight percent, about 0.8 to about 1.5 weight percent, about 0.85 to about 1.5 weight percent, about 0.9 to about 1.5 weight percent, about 0.95 to about 1.5 weight percent, about 1.0 to about 1.5 weight percent, about 1.05 to about 1.5 weight percent, about 1.1 to about 1.5 weight percent, about 1.15 to about 1.5 weight percent, about 1.2 to about 1.5 weight percent, about 1.25 to about 1.5 weight percent, about 1.3 to about 1.5 weight percent, or about 1.4 to about 1.5 weight percent, based on the total weight of the initial reaction mixture.

Any suitable type of catalyst for facilitating the reaction of formamide and acetaldehyde may be used in first reaction zone 20. In some embodiments, the catalyst may be a basic catalyst including, for example, a strongly basic catalyst, a weakly basic catalyst, or a weakly basic salt comprising a strong base and a weak acid. In some embodiments, the catalyst can be a strong non-nucleophilic base in order to prevent undesirable side reactions. The catalyst may be an organic or inorganic base and can, for example, include hydroxides, carbonates, bicarbonates, phosphates, pyrophosphates, and hydrogenphosphates of alkali metals, and/or it may include quarternary ammonium compounds, tertiary amines, ion exchange resins, guanidine derivatives, amidine compounds, and combinations thereof. Specific examples of suitable basic catalysts for use in first reaction zone 20 can include, but are not limited to, potassium carbonate, sodium carbonate, potassium phosphate, sodium phosphate, potassium pyrophosphate, sodium pyrophosphate, potassium bicarbonate, sodium bicarbonate, lithium bicarbonate, potassium hydrogenphosphate, sodium hydrogenphosphate, lithium hydrogenphosphate, trimethylamine, triethylamine tributylamine, diisopropylethylamine, 8-diazabicyclo[5.4.0]undec-7-ene, 1,1,3,3-tetramethylguanidine, and combinations thereof.

One or more of the starting materials in lines 110, 112, and/or 114 may optionally be combined with at least one solvent prior to, or within, first reaction zone 20. When present, the solvent may be added to first reaction zone 20 via a separate line (not shown), or it may be combined with one or more of the starting materials in lines 110, 112, and/or 114. When used, the amount of solvent present in first reaction zone 20 may be at least about 20, at least about 25, at least about 30, at least about 35, at least about 40, or at least about 45 weight percent and/or not more than about 80, not more than about 75, not more than about 70, not more than about 65, not more than about 60, or not more than about 55 weight percent, based on the total weight of the initial reaction mixture.

When used, the solvent can be present in an amount in the range of from about 20 to about 80 weight percent, about 20 to about 75 weight percent, about 20 to about 70 weight percent, about 20 to about 65 weight percent, about 20 to about 60 weight percent, about 20 to about 55 weight percent, about 20 to about 80 weight percent, about 20 to about 75 weight percent, about 20 to about 70 weight percent, about 20 to about 65 weight percent, about 20 to about 60 weight percent, about 20 to about 55 weight percent, about 25 to about 80 weight percent, about 25 to about 75 weight percent, about 25 to about 70 weight percent, about 25 to about 65 weight percent, about 25 to about 60 weight percent, about 25 to about 55 weight percent, about 30 to about 80 weight percent, about 30 to about 75 weight percent, about 30 to about 70 weight percent, about 30 to about 65 weight percent, about 30 to about 60 weight percent, about 30 to about 55 weight percent, about 35 to about 80 weight percent, about 35 to about 75 weight percent, about 35 to about 70 weight percent, about 35 to about 65 weight percent, about 35 to about 60 weight percent, about 35 to about 55 weight percent, about 40 to about 80 weight percent, about 40 to about 75 weight percent, about 40 to about 70 weight percent, about 40 to about 65 weight percent, about 40 to about 60 weight percent, about 40 to about 55 weight percent, about 45 to about 80 weight percent, about 45 to about 75 weight percent, about 45 to about 70 weight percent, about 45 to about 65 weight percent, about 45 to about 60 weight percent, or about 45 to about 55 weight percent, based on the total weight of the initial reaction mixture.

When used, the solvent introduced into first reaction zone 20 may be any suitable type of solvent. The solvent may include a single solvent, or it may comprise a mixture of two or more solvents. In some embodiments, the solvent may be selected based on its solubility with one or more of the starting materials in lines 110, 112, and/or 114, and/or with the reaction product produced within first reaction zone 20. For example, at least one of the starting materials introduced into and/or the product withdrawn from first reaction zone 20 may have a solubility of at least about 20, at least about 25, at least about 30, at least about 35, at least about 40, at least about 45, at least about 50, at least about 55 weight percent in the solvent introduced into first reaction zone 20. In addition, or the alternative, at least one of the reagents introduced into and/or the reaction product withdrawn from first reaction zone 20 may have a solubility of not more than about 80, not more than about 75, not more than about 70, not more than about 65 weight percent in the solvent introduced into first reaction zone 20. Solubility is measured at 20° C. using CIPAC Method MT 181, unless otherwise noted.

At least one of the starting materials introduced into and/or the product withdrawn from first reaction zone 20 may have a solubility in the range of from 20 to about 80 weight percent, about 20 to about 75 weight percent, about 20 to about 70 weight percent, about 20 to about 65 weight percent, about 20 to about 60 weight percent, about 20 to about 55 weight percent, about 20 to about 80 weight percent, about 20 to about 75 weight percent, about 20 to about 70 weight percent, about 20 to about 65 weight percent, about 20 to about 60 weight percent, about 20 to about 55 weight percent, about 25 to about 80 weight percent, about 25 to about 75 weight percent, about 25 to about 70 weight percent, about 25 to about 65 weight percent, about 25 to about 60 weight percent, about 25 to about 55 weight percent, about 30 to about 80 weight percent, about 30 to about 75 weight percent, about 30 to about 70 weight percent, about 30 to about 65 weight percent, about 30 to about 60 weight percent, about 30 to about 55 weight percent, about 35 to about 80 weight percent, about 35 to about 75 weight percent, about 35 to about 70 weight percent, about 35 to about 65 weight percent, about 35 to about 60 weight percent, about 35 to about 55 weight percent, about 40 to about 80 weight percent, about 40 to about 75 weight percent, about 40 to about 70 weight percent, about 40 to about 65 weight percent, about 40 to about 60 weight percent, about 40 to about 55 weight percent, about 45 to about 80 weight percent, about 45 to about 75 weight percent, about 45 to about 70 weight percent, about 45 to about 65 weight percent, about 45 to about 60 weight percent, or about 45 to about 55 weight percent in the solvent introduced into first reaction zone 20. When facility 10 is used to produce N-vinylformamide and a solvent is used in first reaction zone 20, at least one of acetaldehyde, formamide, and 1-hydroxyethylformamide can have a solubility in the selected solvent within one or more of the above ranges.

Suitable solvents may include, for example, polar organic solvents, such as mono-, di-, and/or multi-functional alcohols, or water. In some embodiments, when used, the solvent introduced into first reaction zone 20 can comprise at least one $C_1$ to $C_{20}$ alcohol, at least one $C_1$ to $C_{18}$ alcohol, at least one $C_1$ to $C_{16}$ alcohol, at least one $C_1$ to $C_8$ alcohol, or at least one $C_1$ to $C_4$ alcohol. When present, such alcohols can make up at least about 50, at least about 60, at least about 70, at least about 80, at least about 90, or at least about 95 weight percent, or all of the solvent in first reaction zone 20. Additional examples of suitable solvents can include, but are not limited to, water, methanol, ethanol, isopropanol, isobutanol, butanol, hexanol, heptanol, n-octanol, 2-ethylhexanol, glycerol and combinations thereof. In some embodiments, certain solvents may not be used in first reaction zone 20 and, as a result, these solvents may be present in an amount of not more than about 20, not more than about 15, not more than about 10, not more than about 5, not more than about 2, or not more than about 1 weight percent, based on the total weight of solvent introduced into first reaction zone 20. Examples of solvents not used in first reaction zone 20 can include, for example, aliphatic hydrocarbons such as hexane, cyclohexane, heptane, octane, isooctane, decane, and methylcyclohexane, and aromatic hydrocarbons such as toluene, xylene, benzene, and cyclohexane, and combinations of two or more of the above. In some embodiments, the solvent may not include formamide (or other carboxylic acid amide such as N-methylformamide).

In some embodiments of the present invention, no, or substantially no, solvent is introduced into first reaction zone 20. For example, the total amount of solvent introduced into first reaction zone 20 and/or in the reaction mixture within first reaction zone 20 can be not more than about 20, not more than about 15, not more than about 10, not more than about 5, not more than about 2, or not more than about 1 weight percent, based on the total weight of the initial reaction mixture. In some embodiments when no additional solvent is used, one of the starting materials introduced into first reaction zone 20 via lines 110 and 112 may be present in stoichiometric excess in one or more of the ranges discussed previously.

Upon introduction into first reaction zone 20, at least a portion of the formamide (or other carboxylic acid amide such as N-methylformamide) and acetaldehyde may react in the presence of the basic catalyst to form 1-hydroxyethylformamide (or other 1-hydroxyethylcarboxamide such as N-methyl,1-hydroxyethylformamide). The average temperature of the reaction medium in first reaction zone 20 can be at least about 0, at least about 2, at least about 5, at least about 10, at least about 15, or at least about 20° C. and/or not more than about 55, not more than about 50, not more than about 45, not more than about 40, not more than about 35, not more than about 30, not more than about 25, or not more than about 20° C., or it can be in the range of from about 0 to about 55° C., about 0 to about 50° C., about 0 to about 45° C., about 0 to about 40° C., about 0 to about 35° C., about 0 to about 30° C., about 0 to about 25° C., about 0 to about 20° C., about 2 to about 55° C., about 2 to about 50° C., about 2 to about 45° C., about 2 to about 40° C., about 2 to about 35° C., about 2 to about 30° C., about 2 to about 25° C., about 2 to about 20° C., about 5 to about 55° C., about 5 to about 50° C., about 5 to about 45° C., about 5 to about 40° C., about 5 to about 35° C., about 5 to about 30° C., about 5 to about 25° C., about 5 to about 20° C., about 10 to about 55° C., about 10 to about 50° C., about 10 to about 45° C., about 10 to about 40° C., about 10 to about 35° C., about 10 to about 30° C., about 10 to about 25° C., about 10 to about 20° C., about 15 to about 55° C., about 15 to about 50° C., about 15 to about 45° C., about 15 to about 40° C., about 15 to about 35° C., about 15 to about 30° C., about 15 to about 25° C., about 15 to about 20° C., about 20 to about 55° C., about 20 to about 50° C., about 20 to about 45° C., about 20 to about 40° C., about 20 to about 35° C., about 20 to about 30° C., or about 20 to about 25° C.

The pressure within first reaction zone 20 may be any pressure sufficient to maintain the reaction mixture in the liquid phase and can be, for example, at least about 1, at least about 2, at least about 5, at least about 10 bar gauge and/or not more than about 25, not more than about 20, not more than about 15, or not more than about 12 bar gauge. The pressure may be in the range of from about 1 to about 25 bar gauge, about 1 to about 20 bar gauge, about 1 to about 15 bar gauge, about 1 to about 12 bar gauge, about 2 to about 25 bar gauge, about 2 to about 20 bar gauge, about 2 to about 15 bar gauge, about 2 to about 12 bar gauge, about 5 to about 25 bar gauge, about 5 to about 20 bar gauge, about 5 to about 15 bar gauge, about 5 to about 12 bar gauge, about 10 to about 25 bar gauge, about 10 to about 20 bar gauge, about 10 to about 15 bar gauge, or about 10 to about 12 bar gauge. Other pressures may be suitable depending on the exact composition of the reaction mixture and the specific synthesis reaction being performed.

In some embodiments, the reaction performed in first reaction zone 20 may be a batch reaction, while, in other embodiments, it may be performed in a semi-batch or continuous manner. The reaction may be performed in a single reaction vessel, or it may be carried out in two or more reaction vessels arranged in series or in parallel. Any suitable type of reaction vessel may be employed including, but not limited to, continuous stirred tank reactors, plug flow reactors such as pipe reactors and tubular reactors, and combinations thereof. When performed in two or more vessels, the vessels may be similar types of reaction vessels (e.g., two CSTR reactors in series or parallel), or one or more of the reaction vessels may be different. In some embodiments, the average residence time within first reaction zone 20 can be at least about 2, at least about 5, at least about 10, at least about 15, or at least about 20 minutes and/or not more than about 5, not more than about 3, not more than about 2 hours, not more than about 1 hour, or not more than about 45 minutes. In other embodiments, the average residence time can be at least about 30, at least about 45 minutes, at least about 1 hour, at least about 2, or at least about 2.5 hours and/or not more than about 10, not more than about 8, not more than about 6, or not more than about 4 hours.

The average residence time may be in the range of from about 2 minutes to about 5 hours, about 2 minutes to 3 hours, about 2 minutes to about 2 hours, about 2 minutes to about 1 hour, about 2 minutes to about 45 minutes, about 5 minutes to about 5 hours, about 5 minutes to 3 hours, about 5 minutes to about 2 hours, about 5 minutes to about 1 hour, about 5 minutes to about 45 minutes, about 10 minutes to about 5 hours, about 10 minutes to 3 hours, about 10 minutes to about 2 hours, about 10 minutes to about 1 hour, about 10 minutes to about 45 minutes, about 15 minutes to about 5 hours, about 15 minutes to 3 hours, about 15 minutes to about 2 hours, about 15 minutes to about 1 hour, about 15 minutes to about 45 minutes, about 20 minutes to about 5 hours, about 20 minutes to 3 hours, about 20 minutes to about 2 hours, about 20 minutes to about 1 hour, or about 20 minutes to about 45 minutes.

The average residence time in first reaction zone 20 can be in the range of from about 30 minutes to about 10 hours, about 30 minutes to about 8 hours, about 30 minutes to about 6 hours, about 30 minutes to about 4 hours, about 45 minutes to about 10 hours, about 45 minutes to about 8 hours, about 45 minutes to about 6 hours, about 45 minutes to about 4 hours, about 1 hour to about 10 hours, about 1 hour to about 8 hours, about 1 hour to about 6 hours, about 1 hour to about 4 hours, about 2 hours to about 10 hours, about 2 hours to about 8 hours, about 2 hours to about 6 hours, about 2 hours to about 4 hours, about 2.5 hours to about 10 hours, about 2.5 hours to about 8 hours, about 2.5 hours to about 6 hours, or about 2.5 hours to about 4 hours.

According to various embodiments of the present invention, all, or substantially all, of the reaction product formed in the first reaction zone may remain in solution upon its formation, so that, for example, not more than about 20, not more than about 15, not more than about 10, not more than about 5, not more than about 2, or not more than about 1 percent of the total amount of reaction product crystallizes or precipitates out of solution within first reaction zone 20. In some embodiments, at least about 70, at least about 75, at least about 80, at least about 85, at least about 90, at least about 95, at least about 97, or at least about 99 weight percent, or all, of the reaction product may remain in solution upon its formation. In some cases, the reaction product may be 1-hydroxyethylformamide or it may be any other suitable 1-hydroxyethylcarboxamide such as, for example, N-methyl,1-hydroxyethylformamide. As a result, the total solids content of the reaction mixture within first reaction zone can be not more than about 15, not more than about 10, not more than about 8, not more than about 5, not more than about 3, not more than about 2, not more than about 1, or not more than about 0.5 weight percent. As used herein, the term "total solids content" refers to the concentration, by weight, of solids in a given stream, based on the total weight of the stream. The dry weight of a stream is measured by weighing the residue of a sample after filtration.

Unlike most conventional processes for producing N-vinyl carboxylic acid amides, facility 10 may not include any intervening solids handling steps between first reaction zone 20 and second reaction zone 30. Such solids handling steps absent from facility 10 may include, but are not limited to, crystallization or precipitation, washing, filtration, and redissolving of the intermediate product formed within first reaction zone 20. By maintaining at least about 80, at least about 85, at least about 90, at least about 95, at least about 97, or at least about 99 weight percent of the reaction product formed in first reaction zone 20 in solution, such additional steps may be eliminated. Additionally, steps such as adding seed crystals or cooling of the reaction mixture within first reaction zone 20 may also be omitted, thereby retaining as much of the intermediate reaction product as possible in solution with the reaction medium.

The overall yield achieved by the reaction performed in first reaction zone 20 can be at least about 45, at least about 50, at least about 55, at least about 60, at least about 65, at least about 70, at least about 75, at least about 80, at least about 85, at least about 90, at least about 95, or at least about 97 percent. As used herein, the term "yield" refers to the ratio of the actual yield to the theoretical yield expressed as a percentage. As used herein, the term "theoretical yield," refers to the amount of product expected based on complete reaction of the limiting reagent to the wanted product, and the term "actual yield" refers to the amount of product actually produced. Additionally, the reaction performed within first reaction zone 20 can exhibit a selectivity for the desired reaction product of at least about 80, at least about 85, at least about 90, at least about 95, or at least about 97 percent. When facility 10 is employed for producing N-vinylformamide, the yield and selectivity of 1-hydroxyethylformamide from first reaction zone 20 can fall within one or more of the above ranges. As used herein, the term "selectivity" refers to the molar ratio of the desired end product to the total amount of product formed in a reaction zone. For example, in first reaction zone 20, the selectivity of 1-hydroxyethylformamide can be defined as the ratio of the total moles of 1-hydroxyethylformamide to the total moles of product produced from the one of the reagents introduced into reaction zone 20. Similarly, when facility 10 is used to produce N-methyl,N-vinylformamide, the selectivity of N-methyl,1-hydroxyethylformamide in first reaction zone 20 may be defined as the total moles of N-methyl,1-hydroxyethylformamide to the total moles of product produced from the N-methylformamide introduced into first reaction zone 20. Processes for producing other N-vinyl carboxylic acid amides would have a selectivity of first reaction zone 20 defined in a similar manner.

Upon completion of the reaction in first reaction zone 20, a liquid reaction mixture comprising 1-hydroxyethylformamide (or other 1-hydroxyethylcarboxamide such as N-methyl,1-hydroxyethylformamide) can be withdrawn from first reaction zone 20 via line 116, as shown in FIG. 1. In some embodiments, the reaction mixture can be a single-phase liquid stream, while in other embodiments, it may be a two-phase liquid stream. However, unlike some conventional processes, the stream in line 116 may not be a slurry. In addition to 1-hydroxyethylformamide, the stream in line 116 may further include formamide and, optionally, one or more solvents. When the stream in line 116 includes a solvent, the solvent may be present in an amount of at least about 5, at least about 10, at least about 15, at least about 20, at least about 30, or at least about 40 weight percent, based on the total weight of the stream. The solvent may include one or more of the above-listed solvents and is typically the same as the solvent used in first reaction zone 20, when used. However, as discussed above, in some embodiments, first reaction zone 20 may not utilize a solvent and, in such cases, the stream in line 116 may include not more than about 20, not more than about 15, not more than about 10, not more than about 5, not more than about 2, or not more than about 1 weight percent of a solvent, based on the total weight of the stream.

Additionally, in some embodiments, the reaction mixture withdrawn from first reaction zone 20 via line 116 can include excess formamide (or other carboxylic acid amide such as N-methylformamide). For example, in some embodiments, the stream in line 116 can include at least about 1, at least about 2, at least about 5, at least about 8, at least about 10, at least about 15, at least about 20, at least about 25, or at least about 30 weight percent formamide and/or not more than about 60, not more than about 55, not more than about 50, not more than about 45, not more than about 40, or not more than about 35 weight percent formamide, based on the total weight of the stream in line 116.

The amount of formamide (or other carboxylic acid amide such as N-methylformamide) in the stream withdrawn from first reaction zone 20 in line 116 can be in the range of from about 1 to about 60 weight percent, about 1 to about 55 weight percent, about 1 to about 50 weight percent, about 1 to about 45 weight percent, about 1 to about 40 weight percent, about 1 to about 35 weight percent, about 2 to about 60 weight percent, about 2 to about 55 weight percent, about 2 to about 50 weight percent, about 2 to about 45 weight percent, about 2 to about 40 weight percent, about 2 to about 35 weight percent, about 5 to about 60 weight percent, about 5 to about 55 weight percent, about 5 to about 50 weight percent, about 5 to about 45 weight percent, about 5 to about 40 weight percent, about 5 to about 35 weight percent, about 8 to about 60 weight percent, about 8 to about 55 weight percent, about 8 to about 50 weight percent, about 8 to about 45 weight percent, about 8 to about 40 weight percent, about 8 to about 35 weight percent, about 10 to about 60 weight percent, about 10 to about 55 weight percent, about 10 to about 50 weight percent, about 10 to about 45 weight percent, about 10 to about 40 weight percent, about 10 to about 35 weight percent, about 15 to about 60 weight percent, about 15 to about 55 weight percent, about 15 to about 50 weight percent, about 15 to about 45 weight percent, about 15 to about 40 weight percent, about 15 to about 35 weight percent, about 20 to about 60 weight percent, about 20 to about 55 weight percent, about 20 to about 50 weight percent, about 20 to about 45 weight percent, about 20 to about 40 weight percent, about 20 to about 35 weight percent, about 25 to about 60 weight percent, about 25 to about 55 weight percent, about 25 to about 50 weight percent, about 25 to about 45 weight percent, about 25 to about 40 weight percent, or about 25 to about 35 weight percent, based on the total weight of the stream in line 116.

The molar ratio of formamide (or other carboxylic acid amide such as N-methylformamide) to 1-hydroxyethylformamide (or other 1-hydroxyethylcarboxamide such as N-methyl,1-hydroxyethylformamide) in the stream withdrawn from first reaction zone 20 via line 116 can be at least about 1.05:1, at least about 1.1:1, at least about 1.15:1, or at least about 1.2:1 and/or not more than about 5:1, not more than about 3:1, not more than about 2.5:1, not more than about 2:1, not more than about 1.75:1, or it can be in the range of from about 1.05:1 to about 5:1, about 1.05:1 to about 3:1, about 1.05:1 to about 2.5:1, about 1.05:1 to about 2:1, about 1.05:1 to about 1.75:1, about 1.1:1 to about 5:1, about 1.1:1 to about 3:1, about 1.1:1 to about 2.5:1, about 1.1:1 to about 2:1, about 1.1:1 to about 1.75:1, about 1.15:1 to about 5:1, about 1.15:1 to about 3:1, about 1.15:1 to about 2.5:1, about 1.15:1 to about 2:1, about 1.15:1 to about 1.75:1, about 1.2:1 to about 5:1, about 1.2:1 to about 3:1, about 1.2:1 to about 2.5:1, about 1.2:1 to about 2:1, or about 1.2:1 to about 1.75:1.

Additionally, the reaction mixture withdrawn from first reaction zone 20 via line 116 may include small amounts of other components, such as, for example, unreacted starting material, undesirable side reaction products, residual solvents, and/or catalyst. In some embodiments, the total amount of these other components, including, catalyst, unreacted acetaldehyde, residual solvents, and/or reaction byproducts, if present, can be not more than about 10, not more than about 8, not more than about 5, not more than about 3, not more than about 2, or not more than about 1 weight percent, based on the total weight of the stream in line 116.

In some embodiments, at least a portion of the formamide (or other carboxylic acid amide such as N-methylformamide) introduced into first reaction zone 20 may be recycled from another portion of facility 10. For example, in some embodiments, at least about 10, at least about 20, at least about 30, at least about 40, at least about 50, at least about 60, at least about 70, at least about 80, or at least about 90 weight percent of the total amount of formamide (or other carboxylic acid amide such as N-methylformamide) added to first reaction zone 20 may be recycled from another part of facility 10. In other embodiments, not more than about 40, not more than about 30, not more than about 25, not more than about 20, not more than about 10, or not more than about 5 weight percent of the total amount of formamide (or other carboxylic acid amide such as N-methylformamide) introduced into first reaction zone 20 may be recycled from another part of facility 10.

For example, as shown in FIG. 1, at least a portion of the formamide introduced into first reaction zone 20 via line 110 may originate from a yet-to-be-discussed formamide purification and recycling zones 64 and 74 in line 150, while at least a portion of the formamide introduced into first reaction zone 20 via line 110 may be "fresh" formamide introduced into facility 10 for the first time. In some embodiments, all, or substantially, all of the formamide may be fresh formamide, while, in other embodiments, all, or substantially, all of the formamide may be recycled to first reaction zone 20 via line 150. Otherwise, at least a portion of the formamide introduced into first reaction zone 20 may be fresh, while another portion may be recycled from within facility 10.

Referring back to FIG. 1, the stream in line 116 may subsequently be introduced into a second reaction zone 30. As discussed previously and in direct contrast to conventional processes for producing N-vinylformamide, this can be done without an intervening solids handling step so that a major portion (or all) of the stream withdrawn from first reaction zone 20 in line 116 may be passed in sequence to second reaction zone 30 without any intervening process steps. In some embodiments, at least about 60, at least about 70, at least about 80, at least about 90, or at least about 95 weight percent of the stream withdrawn from first reaction zone 20 via line 116 may be passed to second reaction zone 30 with no intervening process steps, including solids handling steps such as filtration, washing, redissolving, and the like.

Upon introduction into second reaction zone 30, the stream in line 116 may be combined with at least one alcohol in line 118 and an acid catalyst in line 120. The combining may occur in any suitable way and can, for example, include combining the first reaction mixture with an alcohol and/or catalyst in a single conduit prior to introducing the combined stream into a reaction vessel, or may include simultaneously adding the first reaction mixture along with the alcohol, and/or the catalyst into a reaction vessel (not shown). Once combined, at least a portion of the 1-hydroxyethylformamide in the first reaction mixture may be alkoxylated with the alcohol to provide a second reaction mixture comprising 1-alkoxyethylformamide (or other 1-alkoxyethylcarboxamide such as N-methyl,1-alkoxyethylformamide). Although shown in FIG. 1 as being performed in separate reaction zones 20 and 30, it should be understood that the reaction between acetaldehyde and formamide (or other carboxylic acid amide such as N-methylformamide) may be performed in the same reaction vessel as the alkoxylation of 1-hydroxyethylformamide (or other 1-hydroxyethylcarboxamide such as N-methyl,1-hydroxyethylformamide). In such cases with a single reaction vessel is utilized, the alcohol and acid catalyst would simply be added to the first reaction mixture within the reactor at some point during the reaction without removing the first reaction mixture from the vessel. Alternatively, as discussed above, the first reaction mixture may be withdrawn from the first reaction zone 20 and then added to another reactor (not shown) in second reaction zone 30 without any intervening process steps.

In some embodiments, alcohol can be added to the reaction mixture so that the ratio of alcohol added to the second reaction zone 30 in the stream in line 118 to the amount of 1-hydroxyethylformamide (or other 1-hydroxyethylcarboxamide such as N-methyl,1-hydroxyethylformamide) introduced into second reaction zone 30 in stream in line 116 is at least about 0.5:1, at least about 0.6:1, at least about 0.75:1, at least about 0.80:1, at least about 0.90:1, or at least about 1:1 and/or not more than about 3:1, not more than about 2:1, not more than about 1.5:1, not more than about 1.25:1, or not more than about 1.15:1, or it is in the range of from about 0.5:1 to about 3:1, about 0.5:1 to about 2:1, about 0.5:1 to about 1.5:1, about 0.5:1 to about 1.25:1, about 0.5:1 to about 1.15:1, about 0.6:1 to about 3:1, about 0.6:1 to about 2:1, about 0.6:1 to about 1.5:1, about 0.6:1 to about 1.25:1, about 0.6:1 to about 1.15:1, about 0.75:1 to about 3:1, about 0.75:1 to about 2:1, about 0.75:1 to about 1.5:1, about 0.75:1 to about 1.25:1, about 0.75:1 to about 1.15:1, about 0.8:1 to about 3:1, about 0.8:1 to about 2:1, about 0.8:1 to about 1.5:1, about 0.8:1 to about 1.25:1, about 0.8:1 to about 1.15:1, about 0.9:1 to about 3:1, about 0.9:1 to about 2:1, about 0.9:1 to about 1.5:1, about 0.9:1 to about 1.25:1, about 0.9:1 to about 1.15:1, about 1:1 to about 3:1, about 1:1 to about 2:1, about 1:1 to about 1.5:1, about 1:1 to about 1.25:1, or about 1:1 to about 1.15:1.

The alcohol added to the second reaction zone 30 can make up at least about 10, at least about 15, at least about 20, at least about 25, at least about 30, or at least about 35 weight percent and/or not more than about 55, not more than about 50, not more than about 45, not more than about 40 weight percent of the total weight of starting material added to the second reaction zone 30. In some embodiments, this can represent a stoichiometric excess of alcohol above what is needed for the alkoxylation reaction. In some embodiments, the total weight of starting materials would include the first reaction mixture withdrawn from first reaction zone 20 in line 116, the alcohol added to second reaction zone 30 via line 118, and the catalyst added to second reaction zone 30 via line 120.

The alcohol can be present in the second reaction zone 30 in an amount in the range of from about 10 to about 55 weight percent, about 10 to about 50 weight percent, about 10 to about 45 weight percent, about 10 to about 40 weight percent, about 15 to about 55 weight percent, about 15 to about 50 weight percent, about 15 to about 45 weight percent, about 15 to about 40 weight percent, about 20 to about 55 weight percent, about 20 to about 50 weight percent, about 20 to about 45 weight percent, about 20 to about 40 weight percent, about 25 to about 55 weight percent, about 25 to about 50 weight percent, about 25 to about 45 weight percent, about 25 to about 40 weight percent, about 30 to about 55 weight percent, about 30 to about 50 weight percent, about 30 to about 45 weight percent, about 30 to about 40 weight percent, about 35 to about 55 weight percent, about 35 to about 50 weight percent, about 35 to about 45 weight percent, or about 35 to about 40 weight percent, based on the total weight of starting materials added to second reaction zone 30.

The alcohol added to second reaction zone 30 via line 118 can include any compound having a hydroxyl functionality sufficient to participate in the alkoxylation of the 1-hydroxyethylformamide (or other 1-hydroxyethylcarboxamide such as N-methyl,1-hydroxyethylformamide) in second reaction zone 30. In some embodiments, the alcohol added to second reaction zone 30 may include a primary or secondary alcohol, although polyvalent alcohols may be used. Further, the alcohol may include a single type of alcohol or a mixture of two or more alcohols. When a solvent is added to first reaction zone 20, the alcohol in line 118 may the same as or different than the solvent. In some embodiments, the alcohol added to second reaction zone 30 via line 118 may include at least one $C_1$ to $C_{12}$ alcohol, at least one $C_1$ to $C_{10}$ alcohol, or at least one $C_1$ to $C_8$ alcohol. Examples of suitable alcohols can include, but are not limited to, methanol, ethanol, n-propanol, isopropyl alcohol, n-butanol, isobutyl alcohol, 2-butyl alcohol, n-pentanol, n-hexanol, n-heptanol, n-octanol, benzyl alcohol, 2-methoxyethanol, 2-ethoxyethanol, 2-propoxyethanol, 2-butoxyethanol, diethyleneglycol monomethyl ether, ethyleneglycol, propylene glycol, 1,4-butanediol, diethyleneglycol, and combinations thereof. In some embodiments, the alcohol introduced into second reaction zone 30 may be selected from the group consisting of methanol, ethanol, n-propanol, n-butanol, isobutyl alcohol, 2-ethylhexanol, and combinations thereof.

Further, as shown in FIG. 1 and discussed in detail below, at least a portion of the alcohol introduced into second reaction zone 30 may be recycled from another portion of facility 10. For example, in some embodiments, at least about 10, at least about 20, at least about 30, at least about 40, at least about 50, at least about 60, at least about 70, at least about 80, or at least about 90 weight percent of the total amount of alcohol added to second reaction zone 30 may be recycled from another part of facility 10. In other embodiments, not more than about 40, not more than about 30, not more than about 25, not more than about 20, not more than about 10, or not more than about 5 weight percent of the total amount of alcohol introduced second reaction zone 30 may be recycled from another part of facility 10. When recycled alcohol is employed, at least a portion of the alcohol introduced into second reaction zone 30 via line 118 may originate from a yet-to-be-discussed alcohol purification and recycling step 72 in line 119, while at least a portion of the alcohol introduced into second reaction zone 30 via line 118 may be "fresh" alcohol introduced into facility 10 for the first time. In some embodiments, all, or substantially, all of the alcohol may be fresh alcohol from line 117, while, in other embodiments, all, or substantially, all of the alcohol may be recycled to second reaction zone via line 119. Otherwise, at least a portion of the alcohol introduced into second reaction zone 30 may be fresh alcohol, and another portion of the alcohol introduced into second reaction zone 30 may be recycled from another area of facility 10.

As discussed above, at least one acid catalyst may also be added to second reaction zone 30 via line 120. In some embodiments, the amount of acid catalyst added to second reaction zone 30 via line 120 may at least about 0.10, at least about 0.20, at least about 0.25, at least about 0.30, or at least about 0.35 weight percent and/or not more than about 10, not more than about 7.5, not more than about 5, not more than about 3, not more than about 2, not more than about 1.5, not more than about 1.25, not more than about 1 weight percent, based on the total weight of components added to second reaction zone 30. The amount of catalyst added to second reaction zone 30 via line 120 can be in the range of from about 0.10 to about 10 weight percent, about 0.10 to about 7.5 weight percent, about 0.10 to about 5 weight percent, about 0.10 to about 3 weight percent, about 0.10 to about 2 weight percent, about 0.10 to about 1.5 weight percent, about 0.10 to about 1.25 weight percent, about 0.10 to about 1 weight percent, about 0.20 to about 10 weight percent, about 0.20 to about 7.5 weight percent, about 0.20 to about 5 weight percent, about 0.20 to about 3 weight percent, about 0.20 to about 2 weight percent, about 0.20 to about 1.5 weight percent, about 0.20 to about 1.25 weight percent, about 0.20 to about 1 weight percent, about 0.25 to about 10 weight percent, about 0.25 to about 7.5 weight percent, about 0.25 to about 5 weight percent, about 0.25 to about 3 weight percent, about 0.25 to about 2 weight percent, about 0.25 to about 1.5 weight percent, about 0.25 to about 1.25 weight percent, about 0.25 to about 1 weight percent, about 0.30 to about 10 weight percent, about 0.30 to about 7.5 weight percent, about 0.30 to about 5 weight percent, about 0.30 to about 3 weight percent, about 0.30 to about 2 weight percent, about 0.30 to about 1.5 weight percent, about 0.30 to about 1.25 weight percent, about 0.30 to about 1 weight percent, about 0.35 to about 10 weight percent, about 0.35 to about 7.5 weight percent, about 0.35 to about 5 weight percent, about 0.35 to about 3 weight percent, about 0.35 to about 2 weight percent, about 0.35 to about 1.5 weight percent, about 0.35 to about 1.25 weight percent, or about 0.35 to about 1 weight percent, based on the total weight of components added to second reaction zone 30.

Any suitable type of catalyst for facilitating an alkoxylation reaction between the alcohol added via line 118 and the 1-hydroxyethylformamide (or other 1-hydroxyethylcarboxamide such as N-methyl,1-hydroxyethylformamide) introduced into second reaction zone 30 via line 116 may be used. The catalyst may be an acid catalyst such as, for example, a strong acid catalyst or a weak acid catalyst. The catalyst may be organic or inorganic. It may be a homogenous catalyst that is at least partially soluble in the reaction mixture, or a heterogeneous catalyst though which the reaction medium passes. Examples of suitable acid catalyst can include, but are not limited to, mineral acids, organic acids, acidic ion-exchange resins having weak or strong acidity, and solid acid catalysts, such as, for example, ion exchange resins. In some embodiments, the acid catalyst added to second reaction zone 30 via line 120 may be selected from the group consisting of sulfuric acid, hydrochloric acid, nitric acid, hydrobromic acid, sulfonic acid, methanesulfonic acid, ethanesulfonic acid, paratoluenesulfonic acid, cross-linked polystyrenesulfonic acid, and combinations thereof.

Upon introduction into second reaction zone 30, at least a portion of the 1-hydroxyethylformamide (or other 1-hydroxyethylcarboxamide such as N-methyl,1-hydroxyethylformamide) can be alkoxylated in the presence of the alcohol to thereby form a second reaction mixture that includes 1-alkoxyethylformamide (or other 1-alkoxyethylcarboxyamide such as N-methyl,1-alkoxyethylformamide). In some embodiments, when the alcohol is ethanol, the reaction product formed in second reaction zone 30 may include 1-ethoxyethylformamide or N-methyl,1-ethoxyethylformamide. The average temperature of the reaction medium in first reaction zone 20 can be at least about 10, at least about 15, at least about 20, at least about 25, or at least about 30° C. and/or not more than about 60, not more than about 55, not more than about 50, not more than about 45, not more than about 40° C., or it can be in the range of from about 10 to about 60° C., about 10 to about 55° C., about 10 to about 50° C., about 10 to about 45° C., about 10 to about 40° C., about 15 to about 60° C., about 15 to about 55° C., about 15 to about 50° C., about 15 to about 45° C., about 15 to about 40° C., about 20 to about 60° C., about 20 to about 55° C., about 20 to about 50° C., about 20 to about 45° C., about 20 to about 40° C., about 25 to about 60° C., about 25 to about 55° C., about 25 to about 50° C., about 25 to about 45° C., about 25 to about 40° C., about 30 to about 60° C., about 30 to about 55° C., about 30 to about 50° C., about 30 to about 45° C., or about 30 to about 40° C.

The pressure within second reaction zone 30 may be any pressure sufficient to maintain the reaction mixture in the liquid phase and can be at or near atmospheric pressure. In some embodiments, the pressure within second reaction zone 30 may be, for example, at least about 1, at least about 2, or at least about 3 bar gauge and/or not more than about 15, not more than about 12, not more than about 10 bar gauge. The pressure within second reaction zone 30 may be in the range of from about 1 to about 15 bar gauge, about 1 to about 12 bar gauge, about 1 to about 10 bar gauge, or about 1 to about 5 bar gauge, about 2 to about 15 bar gauge, about 2 to about 12 bar gauge, about 2 to about 10 bar gauge, or about 2 to about 5 bar gauge, about 3 to about 15 bar gauge, about 3 to about 12 bar gauge, about 3 to about 10 bar gauge, or about 3 to about 5 bar gauge. Other pressures may be suitable depending on the exact composition of the reaction mixture and the specific synthesis reaction being performed.

In some embodiments, the reaction performed in second reaction zone 30 may be a batch reaction, while, in other embodiments, it may be performed in a semi-batch or continuous manner. The reaction may be performed in a single reaction vessel, or it may be carried out in two or more reaction vessels arranged in series or in parallel. Any suitable type of reaction vessel may be employed including, but not limited to, continuous stirred tank reactors, plug flow reactors such as pipe reactors and tubular reactors, and combinations thereof. When performed in two or more vessels, the vessels may be similar types of reaction vessels (e.g., two CSTR reactors in series or parallel), or one or more of the reaction vessels may be different. In some embodiments, the average residence time within second reaction zone 30 can be at least about 30, at least about 45 minutes, at least about 1 hour, at least about 2, or at least about 2.5 hours and/or not more than about 10, not more than about 8, not more than about 6, or not more than about 4 hours.

The average residence time in second reaction zone 30 can be in the range of from about 30 minutes to about 10 hours, about 30 minutes to about 8 hours, about 30 minutes to about 6 hours, about 30 minutes to about 4 hours, about 45 minutes to about 10 hours, about 45 minutes to about 8 hours, about 45 minutes to about 6 hours, about 45 minutes to about 4 hours, about 1 hour to about 10 hours, about 1 hour to about 8 hours, about 1 hour to about 6 hours, about 1 hour to about 4 hours, about 2 hours to about 10 hours, about 2 hours to about 8 hours, about 2 hours to about 6 hours, about 2 hours to about 4 hours, about 2.5 hours to about 10 hours, about 2.5 hours to about 8 hours, about 2.5 hours to about 6 hours, or about 2.5 hours to about 4 hours.

The overall yield of 1-alkoxyethylformamide (or other 1-alkoxyethylcarboxamide such as N-methyl,1-alkoxyethylformamide) achieved by the reaction performed in second reaction zone 30 can be at least about 80, at least about 85, at least about 90, at least about 92, or at least about 95 percent. As used herein, the term "yield" refers to the ratio of the actual yield to the theoretical yield expressed as a percentage. As used herein, the term "theoretical yield," refers to the amount of product expected based on complete reaction of the limiting reagent to the wanted product, and the term "actual yield" refers to the amount of product actually produced. Additionally, the reaction performed within first reaction zone 20 can exhibit a selectivity for the 1-alkoxyethylformamide (or other 1-alkoxyethylcarboxamide such as N-methyl,1-alkoxyethylformamide) of at least about 80, at least about 85, at least about 90, at least about 95, or at least about 98 percent.

As shown in FIG. 1, upon completion of the reaction, a reaction mixture comprising 1-alkoxyethylformamide (or other 1-alkoxyethylcarboxamide such as N-methyl,1-alkoxyethylformamide) may be withdrawn from second reaction zone 30 via line 122. In some embodiments, the stream in line 122 can include at least about 30, at least about 35, at least about 40, at least about 45 or at least about 50 weight percent 1-alkoxyethylformamide and/or not more than about 90, not more than about 80, not more than about 70, or not more than about 60 weight percent 1-alkoxyethylformamide, or the 1-alkoxyethylformamide may be present in an amount in the range of from about 30 to about 90 weight percent, about 30 to about 80 weight percent, about 30 to about 70 weight percent, about 30 to about 60 weight percent, about 35 to about 90 weight percent, about 35 to about 80 weight percent, about 35 to about 70 weight percent, about 35 to about 60 weight percent, about 40 to about 90 weight percent, about 40 to about 80 weight percent, about 40 to about 70 weight percent, about 40 to about 60 weight percent, about 45 to about 90 weight percent, about 45 to about 80 weight percent, about 45 to about 70 weight percent, about 45 to about 60 weight percent, about 50 to about 90 weight percent about 50 to about 80 weight percent, about 50 to about 70 weight percent, or about 50 to about 60 weight percent.

In addition to the 1-alkoxyethylformamide (or other 1-alkoxyethylcarboxamide such as N-methyl,1-alkoxyethylformamide), the stream in line 122 may also include excess alcohol, along with catalysts, byproducts, and, in some embodiments, excess formamide (or other carboxylic acid amide such as N-methylformamide). In some embodiments, the reaction mixture withdrawn from second reaction zone 30 via line 122 can comprise at least about 5, at least about 10, at least about 15, or at least about 20 weight percent and/or not more than about 50, not more than about 40, not more than about 30 weight percent of an alcohol, based on the total weight of the stream in line 122. Typically, the alcohol in line 122 is the same type of alcohol introduced into second reaction zone 30 via line 118. The amount of alcohol in the reaction mixture in line 122 can be in the range of from about 5 to about 50 weight percent, about 5 to about 40 weight percent, about 5 to about 30 weight percent, about 10 to about 50 weight percent, about 10 to about 40 weight percent, about 10 to about 30 weight percent, about 15 to about 50 weight percent, about 15 to about 40 weight percent, or about 15 to about 30 weight percent, about 20 to about 50 weight percent, about 20 to about 40 weight percent, or about 20 to about 30 weight percent, based on the total weight of the stream in line 122.

In some embodiments, the molar ratio of alcohol to 1-alkoxyethylformide (or other 1-alkoxyethylcarboamide) in the stream in line 122 can be at least about 0.75:1, at least about 0.85:1, at least about 0.95:1, at least about 1:1, at least about 1.1:1, at least about 1.2:1, or at least about 1.3:1 and/or not more than about 5:1, not more than about 3:1, not more than about 2.5:1, not more than about 2.25:1, not more than about 2:1, or not more than about 1.5:1. The molar ratio of alcohol to 1-alkoxyethylformamide in the stream in line 122 can be in the range of from about 0.75:1 to about 5:1, about 0.75:1 to about 3:1, about 0.75:1 to about 2:1, about 0.75:1 to about 2.25:1, about 0.75:1 to about 2:1, about 0.75:1 to about 1.5:1, about 0.85:1 to about 5:1, about 0.85:1 to about 3:1, about 0.85:1 to about 2:1, about 0.85:1 to about 2.25:1, about 0.85:1 to about 2:1, about 0.85:1 to about 1.5:1, about 0.95:1 to about 5:1, about 0.95:1 to about 3:1, about 0.95:1 to about 2:1, about 0.95:1 to about 2.25:1, about 0.95:1 to about 2:1, about 0.95:1 to about 1.5:1, about 1:1 to about 5:1, about 1:1 to about 3:1, about 1:1 to about 2:1, about 1:1 to about 2.25:1, about 1:1 to about 2:1, about 1:1 to about 1.5:1, about 1.1:1 to about 5:1, about 1.1:1 to about 3:1, about 1.1:1 to about 2:1, about 1.1:1 to about 2.25:1, about 1.1:1 to about 2:1, about 1.1:1 to about 1.5:1, about 1.2:1 to about 5:1, about 1.2:1 to about 3:1, about 1.2:1 to about 2:1, about 1.2:1 to about 2.25:1, about 1.2:1 to about 2:1, about 1.2:1 to about 1.5:1, about 1.3:1 to about 5:1, about 1.3:1 to about 3:1, about 1.3:1 to about 2:1, about 1.3:1 to about 2.25:1, about 1.3:1 to about 2:1, or about 1.3:1 to about 1.5:1.

In some embodiments, the reaction mixture withdrawn from second reaction zone 30 in line 122 may also include an excess of formamide (or other carboxylic acid amide such as N-methylformamide). For example, the stream in line 122 may comprise at least about 1, at least about 2, at least about 5, at least about 10, at least about 15, at least about 20 weight percent and/or not more than about 70, not more than about 60, not more than about 50, not more than about 45, not more than about 40, not more than about 35, not more than about 30, or not more than about 25 weight percent formamide, based on the total weight of the reaction mixture in line 122. This is in contrast to many conventional processes, which would include only trace amounts of formamide in the effluent from the second reaction zone 30.

The total amount of formamide in the reaction mixture withdrawn from second reaction zone 30 in line 122 can be in the range of from about 1 to about 70 weight percent, about 1 to about 60 weight percent, about 1 to about 50 weight percent, about 1 to about 45 weight percent, about 1 to about 40 weight percent, about 1 to about 35 weight percent, about 1 to about 30 weight percent, about 1 to about 25 weight percent, about 2 to about 70 weight percent, about 2 to about 60 weight percent, about 2 to about 50 weight percent, about 2 to about 45 weight percent, about 2 to about 40 weight percent, about 2 to about 35 weight percent, about 2 to about 30 weight percent, about 2 to about 25 weight percent, about 5 to about 70 weight percent, about 5 to about 60 weight percent, about 5 to about 50 weight percent, about 5 to about 45 weight percent, about 5 to about 40 weight percent, about 5 to about 35 weight percent, about 5 to about 30 weight percent, about 5 to about 25 weight percent, about 10 to about 70 weight percent, about 10 to about 60 weight percent, about 10 to about 50 weight percent, about 10 to about 45 weight percent, about 10 to about 40 weight percent, about 10 to about 35 weight percent, about 10 to about 30 weight percent, about 10 to about 25 weight percent, about 15 to about 70 weight percent, about 15 to about 60 weight percent, about 15 to about 50 weight percent, about 15 to about 45 weight percent, about 15 to about 40 weight percent, about 15 to about 35 weight percent, about 15 to about 30 weight percent, about 15 to about 25 weight percent, about 20 to about 70 weight percent, about 20 to about 60 weight percent, about 20 to about 50 weight percent, about 20 to about 45 weight percent, about 20 to about 40 weight percent, about 20 to about 35 weight percent, about 20 to about 30 weight percent, or about 20 to about 25 weight percent, based on the total weight of the stream in line 122.

In some embodiments, the molar ratio of formamide (or other carboxylic acid amide such as N-methylformamide) to 1-alkoxyethylformamide (or other 1-alkoxyethylcarboxamide such as N-methyl,1-alkoxyethylformamide) in the stream withdrawn from second reaction zone 30 via line 122 can be at least about 1.05:1, at least about 1.1:1, at least about 1.15:1, at least about 1.2:1, at least about 1.3, or at least about 1.5 and/or not more than about 3:1, not more than about 2.5:1, not more than about 2:1, not more than about 1.75:1, or it can be in the range of from about 1.05:1 to about 3:1, about 1.05:1 to about 2.5:1, about 1.05:1 to about 2:1, about 1.05:1 to about 1.75:1, about 1.1:1 to about 3:1, about 1.1:1 to about 2.5:1, about 1.1:1 to about 2:1, about 1.1:1 to about 1.75:1, about 1.15:1 to about 3:1, about 1.15:1 to about 2.5:1, about 1.15:1 to about 2:1, about 1.15:1 to about 1.75:1, about 1.2:1 to about 3:1, about 1.2:1 to about 2.5:1, about 1.2:1 to about 2:1, about 1.2:1 to about 1.75:1, about 1.3:1 to about 3:1, about 1.3:1 to about 2.5:1, about 1.3:1 to about 2:1, about 1.3:1 to about 1.75:1, about 1.5:1 to about 3:1, about 1.5:1 to about 2.5:1, about 1.5:1 to about 2:1, or about 1.5:1 to about 1.75:1.

Additionally, the reaction mixture withdrawn from second reaction zone 30 via line 122 may include minor amounts of other components, such as, for example, unreacted starting materials, residual solvent, side reaction products, and catalyst. It may also include water, which is a byproduct of the alkoxylation reaction. In some embodiments, the total amount of the components other than the 1-alkoxyethylformamide (or other 1-alkoxyethylcarboxamide such as N-methyl,1-alkoxyethylformamide), ethanol (or other alcohol), and formamide (or other carboxylic acid amide such as N-methylformamide) present in the stream in line 122 can be not more than about 20, not more than about 15, not more than about 10, or not more than about 8 weight percent, based on the total weight of the stream in line 122, with water being present in an amount of at least about 2, at least about 4, at least about 6 weight percent and/or not more than about 12, not more than about 10, or not more than about 8 weight percent. In some embodiments, the stream in line 112 can include water in an amount in the range of from about 2 to about 12 weight percent, about 2 to about 10 weight percent, about 2 to about 8 weight percent, about 4 to about 12 weight percent, about 4 to about 10 weight percent, about 4 to about 8 weight percent, about 6 to about 12 weight percent, about 6 to about 10 weight percent, or about 6 to about 8 weight percent, based on the total weight of the stream in line 122. The other components, such as residual solvents, catalysts, and/or side products, can be present in an amount of not more than about 5, not more than about 3, not more than about 2, or not more than about 1 weight percent, based on the total weight of the stream in line 122.

As shown in FIG. 1, the reaction mixture withdrawn from second reaction zone 30 can be introduced into an intermediate separation zone 40. In the embodiment depicted in FIG. 1, intermediate separation zone 40 includes an alcohol/water distillation column 42, an alcohol purification column 44, and a 1-alkoxyethylformamide distillation column 46. Each of alcohol/water distillation column 42, alcohol purification column 44, 1-alkoxyethylformamide distillation column 46 can comprise any suitable type of distillation column for separating the feed stream introduced into that column into two or more product streams enriched in certain components. One or more columns may include suitable internal components, such as trays, random packing, or structured packing, and may employ as many separation stages as needed in order to achieve the desired separation. One or more of the columns can be flash evaporation or wiped/falling film evaporation columns. Further, although shown as a single column in FIG. 1, it should be understood that similar separations could be performed using two or more columns arranged in series or in parallel. Additional equipment, such as valves, pumps, control valves, reflux condensers, and reboilers, is not shown, but can be included as appropriate and understood by one skilled in the art.

As shown in FIG. 1, the reaction mixture withdrawn from second reaction zone 30 in line 122 can be introduced into alcohol/water distillation column 42, wherein it is separated into an overhead vapor stream in line 124 and a bottoms liquid stream in line 130. The vapor stream in line 124 may be enriched in water and ethanol, while the bottoms stream may be enriched in 1-alkoxyethylformamide (or other 1-alkoxyethylcarboxamide such as N-methyl,1-alkoxyethylformamide) and formamide (or other carboxylic acid amide such as N-methylformamide). As used herein, the term "enriched" refers to a separated stream that includes at least 50 percent of the total amount of a given component originally present in the stream from which it was separated. For example, a stream withdrawn from a distillation column enriched in component X includes at least 50 percent of the total weight of component X that was introduced into that distillation column.

In some embodiments, the overhead stream withdrawn from alcohol/water distillation column 42 in line 124 includes at least about 55, at least about 60, at least about 65, at least about 70, at least about 75, at least about 80, at least about 85, or at least about 90 percent of the total amount of water and/or ethanol introduced into alcohol/water distillation column 42. Similarly, in some embodiments, the bottoms liquid stream in line 130 can include at least about 55, at least about 60, at least about 65, at least about 70, at least about 75, at least about 80, at least about 85, or at least about 90 percent of the total amount of formamide and/or 1-alkoxyethylformamide introduced into alcohol/water distillation column 42.

The overhead stream withdrawn from alcohol/water distillation column 42 in line 124 can include at least about 50, at least about 60, at least about 65, at least about 70, at least about 75, at least about 80, at least about 85, at least about 90, at least about 95 weight percent of alcohol and water, based on the total weight of the stream in line 124. Individually, the alcohol and water may be present in an amount of at least about 20, at least about 25, at least about 30, at least about 35, at least about 40 weight percent and/or not more than about 70, not more than about 65, not more than about 60, not more than about 55, not more than about 50, not more than about 45, or not more than about 40 weight percent, or an amount in the range of from about 20 to about 70 weight percent, about 20 to about 65 weight percent, about 20 to about 60 weight percent, about 20 to about 55 weight percent, about 20 to about 50 weight percent, about 20 to about 45 weight percent, about 20 to about 40 weight percent, about 25 to about 70 weight percent, about 25 to about 65 weight percent, about 25 to about 60 weight percent, about 25 to about 55 weight percent, about 25 to about 50 weight percent, about 25 to about 45 weight percent, about 25 to about 40 weight percent, about 30 to about 70 weight percent, about 30 to about 65 weight percent, about 30 to about 60 weight percent, about 30 to about 55 weight percent, about 30 to about 50 weight percent, about 30 to about 45 weight percent, about 30 to about 40 weight percent, about 35 to about 70 weight percent, about 35 to about 65 weight percent, about 35 to about 60 weight percent, about 35 to about 55 weight percent, about 35 to about 50 weight percent, about 35 to about 45 weight percent, about 35 to about 40 weight percent, about 40 to about 70 weight percent, about 40 to about 65 weight percent, about 40 to about 60 weight percent, about 40 to about 55 weight percent, about 40 to about 50 weight percent, about 40 to about 45 weight percent, based on the total weight of the stream in line 124.

The bottoms stream withdrawn from alcohol/water distillation column 42 in line 130 can include at least about 50, at least about 60, at least about 65, at least about 70, at least about 75, at least about 80, at least about 85, at least about 90, at least about 95 weight percent of 1-alkoxyethylformamide (or other 1-alkoxyethylcarboxamide such as N-methyl, 1-alkoxyethylformamide) and formamide (or other carboxylic acid amide such as N-methylformamide), based on the total weight of the stream in line 130. Individually, the 1-alkoxyethylformamide and formamide may be present in an amount of at least about 20, at least about 25, at least about 30, at least about 35, at least about 40 weight percent and/or not more than about 70, not more than about 65, not more than about 60, not more than about 55, not more than about 50, not more than about 45, or not more than about 40 weight percent, or an amount in the range of from about 20 to about 70 weight percent, about 20 to about 65 weight percent, about 20 to about 60 weight percent, about 20 to about 55 weight percent, about 20 to about 50 weight percent, about 20 to about 45 weight percent, about 20 to about 40 weight percent, about 25 to about 70 weight percent, about 25 to about 65 weight percent, about 25 to about 60 weight percent, about 25 to about 55 weight percent, about 25 to about 50 weight percent, about 25 to about 45 weight percent, about 25 to about 40 weight percent, about 30 to about 70 weight percent, about 30 to about 65 weight percent, about 30 to about 60 weight percent, about 30 to about 55 weight percent, about 30 to about 50 weight percent, about 30 to about 45 weight percent, about 30 to about 40 weight percent, about 35 to about 70 weight percent, about 35 to about 65 weight percent, about 35 to about 60 weight percent, about 35 to about 55 weight percent, about 35 to about 50 weight percent, about 35 to about 45 weight percent, about 35 to about 40 weight percent, about 40 to about 70 weight percent, about 40 to about 65 weight percent, about 40 to about 60 weight percent, about 40 to about 55 weight percent, about 40 to about 50 weight percent, about 40 to about 45 weight percent, based on the total weight of the stream in line 130.

The maximum temperature of the bottoms stream withdrawn from alcohol/water distillation column 42 in line 130 can be not more than about 150, not more than about 145, not more than about 140, or not more than about 130° C. In some embodiments, maintaining a temperature within the above ranges may minimize degradation of the products, including, for example, the 1-alkoxyethylformamide.

In addition to the above components, the overhead stream withdrawn from alcohol/water distillation column 42 in line 124 and the bottoms stream withdrawn from alcohol/water distillation column 42 in line 130 may include one or more other components, including, for example, unreacted starting materials, side reaction products, and catalysts. Whether these other components are withdrawn from alcohol/water distillation column 42 via the overhead stream in line 124 or the bottoms stream in line 130 depends on the volatility of the components relative to the other components of the system, which may vary depending on the specific reactants, catalysts, and solvents utilized in first and second separation zones 20 and 30. In some embodiments, the overhead stream in line 124 and/or the bottoms stream in line 130 can include not more than about 10, not more than about 8, not more than about 6, not more than about 4, not more than about 2, or not more than about 1 weight percent of components other than the water, alcohol, formamide (or other carboxylic acid amide such as N-methylformamide), and/or 1-alkoxyethylformamide (or other 1-alkoxyethylcarboxamide such as N-methyl,1-alkoxyethylformamide) present in the stream.

As shown in FIG. 1, after being withdrawn from alcohol/water distillation column 42, the overhead stream in line 124 can be introduced into alcohol purification column 44, wherein it is separated into an alcohol-enriched overhead stream in line 126 and a bottoms stream in line 128. In some embodiments, the overhead stream in line 126 can include at least about 50, at least about 55, at least about 60, at least about 65, at least about 70, at least about 75, at least about 80, at least about 85, at least about 90, or at least about 95 weight percent of the total amount of alcohol introduced into alcohol purification column 44 in line 124, while the bottoms stream in line 128 can include at least about 50, at least about 55, at least about 60, at least about 65, at least about 70, at least about 75, at least about 80, or at least about 85 weight percent of the water introduced into alcohol purification column 44 in line 124. Depending on the type and amount of alcohol present in the stream in line 124, alcohol/water distillation column 42 may be an azeotropic distillation column for separating an alcohol-water azeotrope in the overhead stream in line 126 from water and other less volatile components in the bottoms stream in line 128.

The overhead stream in line 126 can include at least about 50, at least about 55, at least about 60, at least about 65, at least about 70, at least about 75, at least about 80, at least about 85, at least about 90, or at least about 95 weight percent alcohol, based on the total weight of the stream, and may further include water and other lighter components in similar amounts. In some embodiments, the overhead vapor stream in line 126 can include not more than about 15, not more than about 10, not more than about 8, not more than about 5, not more than about 3, or not more than about 1 weight percent of components other than alcohol and water, based on the total weight of the stream. Similarly, the bottoms stream in line 128 may include at least about 50, at least about 55, at least about 60, at least about 65, at least about 70, at least about 75, at least about 80, at least about 85, at least about 90, or at least about 95 weight percent water, based on the total weight of the stream, with other components making up not more than about 10, not more than about 8, not more than about 5, not more than about 3, or not more than about 1 weight percent of the stream. The stream in line 128 can be routed to further processing, storage, reuse, or disposal, depending on its specific composition.

As shown in FIG. 1, the overhead stream withdrawn from alcohol purification column 44 in line 126 may be routed to an alcohol recycle and recovery zone 72, wherein at least a portion of the stream may undergo further processing steps to purify the alcohol for subsequent reuse. Any suitable processes can be used to separate out any residual water, catalyst, or other components, such that the stream withdrawn from alcohol recycle and recovery zone 72 in line 119 includes at least about 80, at least about 85, at least about 90, at least about 95, at least about 97, or at least about 99 weight percent alcohol, based on the total weight of the stream in line 119. As shown in FIG. 1, the stream in line 119 may be subsequently returned to second reaction zone 30, wherein all or a portion of the alcohol may be used for the alkoxylation of 1-hydroxyethylformamide as described previously. In some embodiments, at least about 30, at least about 40, at least about 50, at least about 60, at least about 70, at least about 80, at least about 90, or at least about 95 percent of the total weight of alcohol introduced into second reaction zone 30 may be recycled from alcohol recycle and recovery zone 72.

Referring again to alcohol/water separation column 42 shown in FIG. 1, the bottoms liquid stream in line 130 can optionally be combined with a catalyst deactivation component in line 132. The catalyst deactivation component stream in line 132 can include any compound suitable for neutralizing or deactivating residual catalyst remaining the in the stream in line 130. For example, in some embodiments, an acid catalyst, such as, for example sulfuric acid, from second reaction zone 30 may be present in the stream in line 130 and a basic component, such as, for example, sodium carbonate, sodium hydroxide, potassium hydroxide, or ammonia, may be added to neutralize and deactivate the catalyst. Conversely, if the catalyst remaining in line 130 is a basic catalyst, the catalyst deactivation component in line 132 may be an acid. The amount of catalyst deactivation component added in line 132 depends on the type and amount of catalyst present, but is usually enough sufficient to deactivate the catalyst for subsequent removal in a downstream separation zone. In some embodiments, the pH of the combined stream in line 134 can be at least about 4, at least about 4.5, at least about 5 and/or not more than about 9, not more than about 8.5, not more than about 8, or in the range of from about 4 to about 9, about 4 to about 8.5, about 4 to about 8, about 4.5 to about 9, about 4.5 to about 8.5, about 4.5 to about 8, about 5 to about 9, about 5 to about 8.5, or about 5 to about 8.

As shown in FIG. 1, the combined stream in line 134 can then be introduced into 1-alkoxyethylformamide distillation column 46, wherein it can be separated into an overhead product enriched in 1-alkoxyethylformamide (or other 1-alkoxyethylcarboxamide such as N-methyl,1-alkoxyethylformamide) and including formamide (or other carboxylic acid amide such as N-methylformamide) in line 138 and a bottoms stream enriched in deactivated catalyst and other byproducts in line 136.

The 1-alkoxyethylformamide distillation column 46 may be operated under any suitable conditions capable of achieving the desired separation. In some embodiments, the 1-alkoxyethylformamide distillation column 46 may have an overhead temperature of at least about 60, at least about 75, at least about 90, at least about 95, at least about 100, at least about 105° C. and/or not more than about 150° C., not more than about 130, not more than about 125, not more than about 120, not more than about 115, or not more than about 110° C., or it can be in the range of from about 60° C. to about 150° C., about 60° C. to about 130° C., about 60° C. to about 125° C., about 60° C. to about 120° C., about 60° C. to about 115° C., about 60° C. to about 110° C., about 75° C. to about 150° C., about 75° C. to about 130° C., about 75° C. to about 125° C., about 75° C. to about 120° C., about 75° C. to about 115° C., about 75° C. to about 110° C., about 90° C. to about 150° C., about 90° C. to about 130° C., about 90° C. to about 125° C., about 90° C. to about 120° C., about 90° C. to about 115° C., about 90° C. to about 110° C., about 95° C. to about 150° C., about 95° C. to about 130° C., about 95° C. to about 125° C., about 95° C. to about 120° C., about 95° C. to about 115° C., about 95° C. to about 110° C., about 100° C. to about 150° C., about 100° C. to about 130° C., about 100° C. to about 125° C., about 100° C. to about 120°

C., about 100° C. to about 115° C., about 100° C. to about 110° C., about 105° C. to about 150° C., about 105° C. to about 130° C., about 105° C. to about 125° C., about 105° C. to about 120° C., about 105° C. to about 115° C., or about 105° C. to about 110° C.

The overhead pressure of 1-alkoxyethylformamide distillation column 46 can be at least about 1, at least about 2, at least about 5, or at least about 8 mbar absolute (mbara) and/or not more than about 25, not more than about 20, or not more than about 15 mbara, or it can be in the range of from about 1 mbara to about 25 mbara, about 1 mbara to about 20 mbara, about 1 to about 15 mbara, about 2 mbara to about 25 mbara, about 2 mbara to about 20 mbara, about 2 mbara to about 15 mbara, about 5 mbara to about 25 mbara, about 5 mbara to about 20 mbara, about 5 mbara to about 15 mbara, about 8 mbara to about 25 mbara, about 8 mbara to about 20 mbara, or about 8 mbara to about 15 mbara.

The bottoms stream withdrawn from 1-alkoxyethylformamide distillation column 46 in line 136 may include various components, including byproducts and residual components such as, for example, deactivated catalyst. It may be sent to a downstream unit (not shown) for further processing and/or disposal. The overhead product stream in line 138, which can include at least about 70, at least about 80, at least about 85, at least about 90, at least about 95, at least about 97, or at least about 99 percent of the total amount of 1-alkoxyethylformamide and/or formamide introduced into 1-alkoxyethylformamide distillation column 46, may be routed to a pyrolysis unit (not shown) in pyrolysis zone 50, as shown in FIG. 1. In some embodiments, an azeotrope may be formed between the 1-alkoxyethylformamide and formamide and, as a result, a substantial portion, nearly all, or all of the formamide introduced into 1-alkoxyethylformamide distillation column 46 may be withdrawn in the overhead stream in line 138. The overhead stream in line 138 can comprise at least about 35, at least about 40, at least about 45, at least about 50, at least about 55 and/or not more than about 90, not more than about 85, not more than about 80, not more than about 75, or not more than about 70 weight percent of 1-alkoxyethylformamide, based on the total weight of the stream.

The overhead stream withdrawn from 1-alkoxyethylformamide distillation column 46 in line 138 can include 1-alkoxyethylformamide (or other 1-alkoxyethylcarboxamide such as N-methyl,1-alkoxyethylformamide) in an amount in the range of from about 35 to about 90 weight percent, at least about 35 to at least about 85 weight percent, at least about 35 to at least about 80 weight percent, at least about 35 to at least about 75 weight percent, at least about 35 to at least about 70 weight percent, at least about 40 to at least about 85 weight percent, at least about 40 to at least about 80 weight percent, at least about 40 to at least about 75 weight percent, at least about 40 to at least about 70 weight percent, at least about 45 to at least about 85 weight percent, at least about 45 to at least about 80 weight percent, at least about 45 to at least about 75 weight percent, at least about 45 to at least about 70 weight percent, at least about 50 to at least about 85 weight percent, at least about 50 to at least about 80 weight percent, at least about 50 to at least about 75 weight percent, at least about 50 to at least about 70 weight percent, at least about 55 to at least about 85 weight percent, at least about 55 to at least about 80 weight percent, at least about 55 to at least about 75 weight percent, or at least about 55 to at least about 70 weight percent, based on the total weight of the stream in line 138.

In some embodiments, the overhead stream withdrawn from 1-alkoxyethylformamide distillation column 46 in line 138 may also include excess formamide (or other carboxylic acid amide such as N-methylformamide). For example, the stream in line 138 may comprise at least about 5, at least about 10, at least about 15, at least about 20, at least about 25, at least about 30 weight percent and/or not more than about 70, not more than about 60, not more than about 50, not more than about 45, not more than about 40, not more than about 35, not more than about 30, or not more than about 25 weight percent formamide, based on the total weight of the reaction mixture in line 138. This is in contrast to many conventional processes, which would include only trace amounts of formamide, if any, in the overhead stream withdrawn from 1-alkoxyethylformamide distillation column 46 in line 138.

The total amount of formamide (or other carboxylic acid amide such as N-methylformamide) in the overhead stream withdrawn from 1-alkoxyethylformamide distillation column 46 in line 138 can be in the range of from about 1 to about 70 weight percent, about 1 to about 60 weight percent, about 1 to about 50 weight percent, about 1 to about 45 weight percent, about 1 to about 40 weight percent, about 1 to about 35 weight percent, about 1 to about 30 weight percent, about 1 to about 25 weight percent, about 2 to about 70 weight percent, about 2 to about 60 weight percent, about 2 to about 50 weight percent, about 2 to about 45 weight percent, about 2 to about 40 weight percent, about 2 to about 35 weight percent, about 2 to about 30 weight percent, about 2 to about 25 weight percent, about 5 to about 70 weight percent, about 5 to about 60 weight percent, about 5 to about 50 weight percent, about 5 to about 45 weight percent, about 5 to about 40 weight percent, about 5 to about 35 weight percent, about 5 to about 30 weight percent, about 5 to about 25 weight percent, about 10 to about 70 weight percent, about 10 to about 60 weight percent, about 10 to about 50 weight percent, about 10 to about 45 weight percent, about 10 to about 40 weight percent, about 10 to about 35 weight percent, about 10 to about 30 weight percent, about 10 to about 25 weight percent, about 15 to about 70 weight percent, about 15 to about 60 weight percent, about 15 to about 50 weight percent, about 15 to about 45 weight percent, about 15 to about 40 weight percent, about 15 to about 35 weight percent, about 15 to about 30 weight percent, about 15 to about 25 weight percent, about 20 to about 70 weight percent, about 20 to about 60 weight percent, about 20 to about 50 weight percent, about 20 to about 45 weight percent, about 20 to about 40 weight percent, about 20 to about 35 weight percent, about 20 to about 30 weight percent, about 20 to about 25 weight percent, about 25 to about 70 weight percent, about 25 to about 60 weight percent, about 25 to about 50 weight percent, about 25 to about 45 weight percent, about 25 to about 40 weight percent, about 25 to about 35 weight percent, about 25 to about 30 weight percent, about 30 to about 70 weight percent, about 30 to about 60 weight percent, about 30 to about 50 weight percent, about 30 to about 45 weight percent, about 30 to about 40 weight percent, or about 30 to about 35 weight percent, based on the total weight of the stream in line 138.

In some embodiments, the molar ratio of formamide (or other carboxylic acid amide such as N-methylformamide) to 1-alkoxyethylformamide (or other 1-alkoxyethylcarboxamide such as N-methyl,1-alkoxyethylformamide) in the stream in line 138 can be at least about 0.3:1, at least about 0.5:1, at least about 0.75:1, at least about 1:1, at least about 1.05:1, at least about 1.1:1, at least about 1.15:1, at least about 1.2:1, at least about 1.3, or at least about 1.5 and/or not more than about 3:1, not more than about 2.5:1, not more than about 2:1, not more than about 1.75:1, or it can be in the range of from about 0.3:1 to about 3:1, about 0.3:1 to about 2.5:1, about 0.3:1 to about 2:1, about 0.3:1 to about 1.75:1, about 0.5:1 to about 3:1, about 0.5:1 to about 2.5:1, about 0.5:1 to about 2:1, about 0.5:1 to about 1.75:1, about 0.75:1 to about 3:1, about 0.75:1 to about 2.5:1, about 0.75:1 to about 2:1, about 0.75:1 to about 1.75:1, about 1:1 to about 3:1, about 1:1 to about 2.5:1, about 1:1 to about 2:1, about 1:1 to about 1.75:1, about 1.05:1 to about 3:1, about 1.05:1 to about 2.5:1, about 1.05:1 to about 2:1, about 1.05:1 to about 1.75:1, about 1.1:1 to about 3:1, about 1.1:1 to about 2.5:1, about 1.1:1 to about 2:1, about 1.1:1 to about 1.75:1, about 1.15:1 to about 3:1, about 1.15:1 to about 2.5:1, about 1.15:1 to about 2:1, about 1.15:1 to about 1.75:1, about 1.2:1 to about 3:1, about 1.2:1 to about 2.5:1, about 1.2:1 to about 2:1, about 1.2:1 to about 1.75:1, about 1.3:1 to about 3:1, about 1.3:1 to about 2.5:1, about 1.3:1 to about 2:1, about 1.3:1 to about 1.75:1, about 1.5:1 to about 3:1, about 1.5:1 to about 2.5:1, about 1.5:1 to about 2:1, or about 1.5:1 to about 1.75:1.

Additionally, the overhead product stream in line 138 may include minor amounts of other components, such as, for example, unreacted starting materials, residual solvent, side reaction products, and catalyst. In some embodiments, the total amount of the components other than the 1-alkoxyethylformamide (or other 1-alkoxyethylcarboxamide such as N-methyl,1-alkoxyethylformamide) and formamide (or other carboxylic acid amide such as N-methylformamide) in the stream in line 138 can be not more than about 20, not more than about 15, not more than about 10, or not more than about 8, not more than about 5, not more than about 3, not more than about 2, not more than about 1, not more than about 0.5, or not more than about 0.1 weight percent, based on the total weight of the stream in line 138.

As shown in FIG. 1, the overhead product stream withdrawn from 1-alkoxyethylformamide distillation column 46 in line 138 may be routed to pyrolysis zone 50. Pyrolysis zone 50 may include any suitable process to chemically and/or thermally decompose at least a portion of the 1-alkoxyethylformamide (or other 1-alkoxyethylcarboxamide such as N-methyl,1-alkoxyethylformamide) to thereby form N-vinylformamide (or other N-vinyl carboxylic acid amide such as N-methyl,N-vinylformamide) and an alcohol byproduct. Typically, the pyrolysis reaction may be performed in the gas phase, so facility 10 may also include one or more heat exchangers (not shown) upstream of pyrolysis zone 50 for vaporizing at least a portion of the feed stream in line 138. Alternatively, or in addition, the heating may be performed within the pyrolysis reaction vessel (not shown).

The pyrolysis reaction can be carried out at a temperature of at least about 200, at least about 250, at least about 300, at least about 325° C. and/or not more than about 500, not more than about 450, not more than about 400, or not more than about 375° C., or at a temperature in the range of from about 200° C. to about 500° C., about 200° C. to about 450° C., about 200° C. to about 400° C., about 200° C. to about 375° C., about 250° C. to about 500° C., about 250° C. to about 450° C., about 250° C. to about 400° C., about 250° C. to about 375° C., about 300° C. to about 500° C., about 300° C. to about 450° C., about 300° C. to about 400° C., about 300° C. to about 375° C., about 350° C. to about 500° C., about 350° C. to about 450° C., about 350° C. to about 400° C., or about 350° C. to about 375° C.

The pressure within pyrolysis zone can be at least about 20, at least about 40, or at least about 50 mbar and/or not more than about 1000, not more than about 750, or not more than about 500 mbar, or it can be in the range of from about 20 mbar to about 1000 mbar, about 20 mbar to about 750 mbar, about 20 mbar to about 500 mbar, about 40 mbar to about 1000 mbar, about 40 mbar to about 750 mbar, about 40 mbar to about 500 mbar, about 50 mbar to about 1000 mbar, about 50 mbar to about 750 mbar, or about 50 mbar to about 500 mbar. The pyrolysis reaction can be carried out for a total reaction time of at least about 0.1, at least about 1, at least about 2, at least about 5, at least about 10, at least about 20, at least about 30 seconds and/or not more than about 90, not more than about 60, not more than about 45 seconds, or in the range of from about 0.1 to about 90 seconds, about 0.1 to about 60 seconds, about 0.1 to about 45 seconds, about 1 to about 90 seconds, about 1 to about 60 seconds, about 1 to about 45 seconds, about 2 to about 90 seconds, about 2 to about 60 seconds, about 2 to about 45 seconds, about 5 to about 90 seconds, about 5 to about 60 seconds, about 5 to about 45 seconds, about 5 to about 90 seconds, about 5 to about 60 seconds, about 5 to about 45 seconds, about 10 to about 90 seconds, about 10 to about 60 seconds, about 10 to about 45 seconds, about 20 to about 90 seconds, about 20 to about 60 seconds, about 20 to about 45 seconds, about 30 to about 90 seconds, about 30 to about 60 seconds, about 30 to about 45 seconds.

Any suitable type of reaction vessel may be used to carry out the pyrolysis reaction in pyrolysis zone 50. In some embodiments, two or more reaction vessels may be used in series or in parallel, or a single vessel may be employed. The pyrolysis reaction can be performed in a continuous, batch, or semi-batch reaction vessel and may be carried out in the gas phase. In some embodiments, when the pyrolysis reaction performed in pyrolysis zone 50 includes chemical pyrolysis, pyrolysis zone 50 may further include at least one heterogeneous catalyst for facilitating the reaction. The catalyst may be arranged in a fixed bed reactor or a fluidized bed reactor, and may be present in any suitable amount needed to achieve the desired conversion. Examples of suitable catalysts can include, but are not limited to, metal oxides (such as magnesium oxide, zinc oxides, copper oxides, titanium oxides), metal hydroxides (such as calcium hydroxide, barium hydroxide) zeolites, metal carbonates and silica-alumina. In some embodiments when the pyrolysis reaction performed in pyrolysis zone 50 is only a thermal pyrolysis reaction, the pyrolysis zone may not include a catalyst.

The overall yield achieved by the reaction performed in pyrolysis zone 50 can be at least about 80, at least about 85, at least about 90, at least about 95, or at least about 97 percent. As used herein, the term "yield" refers to the ratio of the actual yield to the theoretical yield expressed as a percentage. As used herein, the term "theoretical yield," refers to the amount of product expected based on complete reaction of the limiting reagent to the wanted reaction product, and the term "actual yield" refers to the amount of product actually produced. Additionally, the reaction performed within pyrolysis zone 50 can exhibit a selectivity for the desired reaction product of at least about 80, at least about 85, at least about 90, at least about 95, or at least about 97 percent. When facility 10 is employed for producing N-vinylformamide, the yield and selectivity of N-vinylformamide from pyrolysis zone 50 can fall within one or more of the above ranges. The selectivity of pyrolysis zone 50 may defined as the molar ratio of N-vinylformamide to the total moles of reaction products formed from the 1-alkoxyethylformamide introduced into pyrolysis zone 50 present in the crude product stream withdrawn from pyrolysis zone 50 in line 140.

The crude product stream withdrawn from pyrolysis zone 50 in line 140 may include, for example, N-vinylformamide, formamide, and ethanol, along with trace amounts of one or more other components, including byproducts and other residual materials. Optionally, prior to being introduced into final separation zone 60, the stream in line 140 may be passed through a condenser (not shown). When present, the condenser may cool and at least partially condense the gas-phase product stream withdrawn from pyrolysis zone 50 so that at least a portion of the less volatile components, such as N-vinylformamide (or other N-vinyl carboxylic acid amide such as N-methyl,N-vinylformamide) and formamide (or other carboxylic acid amide such as N-methylformamide), may liquefy, while at least a portion of the more volatile components, such as the alcohol, remain in the vapor phase. In some embodiments, part of the alcohol vapor phase can be recycled over the pyrolysis section in order to facilitate the evaporation of fresh pyrolysis feed stream in line 138 (not shown in FIG. 1).

In some embodiments, the stream withdrawn from pyrolysis zone 50 via line 140 can comprise at least about 40, at least about 50, at least about 60, or at least about 70 weight percent N-vinylformamide, based on the total weight of the stream. Additionally, or in the alternative, the stream in line 140 can include not more than about 99, not more than about 95, not more than about 90, not more than about 85, not more than about 80, or not more than about 75 weight percent N-vinylformamide (or other N-vinyl carboxylic acid amide such as N-methyl,N-vinylformamide), based on the total weight of the stream. The stream in line 140 can include N-vinylformamide in an amount in the range of from about 40 to about 99 weight percent, about 40 to about 95 weight percent, about 40 to about 90 weight percent, about 40 to about 85 weight percent, about 40 to about 80 weight percent, about 40 to about 75 weight percent, about 50 to about 99 weight percent, about 50 to about 95 weight percent, about 50 to about 90 weight percent, about 50 to about 85 weight percent, about 50 to about 80 weight percent, about 50 to about 75 weight percent, about 60 to about 99 weight percent, about 60 to about 95 weight percent, about 60 to about 90 weight percent, about 60 to about 85 weight percent, about 60 to about 80 weight percent, about 60 to about 75 weight percent, about 70 to about 99 weight percent, about 70 to about 95 weight percent, about 70 to about 90 weight percent, about 70 to about 85 weight percent, about 70 to about 80 weight percent, or about 70 to about 75 weight percent, based on the total weight of the stream in line 140.

The crude product stream in line 140 may also include an excess of formamide (or other carboxylic acid amide such as N-methylformamide). Although not wishing to be bound by theory, it is hypothesized that the presence of formamide (or other carboxylic acid amide such as N-methylformamide) in the crude product stream may help stabilize the N-vinylformamide (or other N-vinyl carboxylic acid amide such as N-methyl,N-vinylformamide). For example, the stream in line 140 may comprise at least about 1, at least about 2, at least about 5, at least about 10, at least about 15, at least about 20, at least about 25, at least about 30 weight percent and/or not more than about 70, not more than about 60, not more than about 50, not more than about 45, not more than about 40, not more than about 35, not more than about 30, or not more than about 25 weight percent formamide, based on the total weight of the crude product stream in line 140. This is in contrast to many conventional processes, which would include only trace amounts of formamide, if any, in the effluent from pyrolysis zone 50.

The total amount of formamide in the crude product mixture withdrawn from pyrolysis zone 50 in line 140 can be in the range of from about 1 to about 70, about 1 to about 60, about 1 to about 50, about 1 to about 45 weight percent, about 1 to about 40 weight percent, about 1 to about 35 weight percent, about 1 to about 30 weight percent, about 1 to about 25 weight percent, about 2 to about 70 weight percent, about 2 to about 60 weight percent, about 2 to about 50 weight percent, about 2 to about 45 weight percent, about 2 to about 40 weight percent, about 2 to about 35 weight percent, about 2 to about 30 weight percent, about 2 to about 25 weight percent, about 5 to about 70 weight percent, about 5 to about 60 weight percent, about 5 to about 50 weight percent, about 5 to about 45 weight percent, about 5 to about 40 weight percent, about 5 to about 35 weight percent, about 5 to about 30 weight percent, about 5 to about 25 weight percent, about 10 to about 70 weight percent, about 10 to about 60 weight percent, about 10 to about 50 weight percent, about 10 to about 45 weight percent, about 10 to about 40 weight percent, about 10 to about 35 weight percent, about 10 to about 30 weight percent, about 10 to about 25 weight percent, about 15 to about 70 weight percent, about 15 to about 60 weight percent, about 15 to about 50 weight percent, about 15 to about 45 weight percent, about 15 to about 40 weight percent, about 15 to about 35 weight percent, about 15 to about 30 weight percent, about 15 to about 25 weight percent, about 20 to about 70 weight percent, about 20 to about 60 weight percent, about 20 to about 50 weight percent, about 20 to about 45 weight percent, about 20 to about 40 weight percent, about 20 to about 35 weight percent, about 20 to about 30 weight percent, about 20 to about 25 weight percent, about 25 to about 70 weight percent, about 25 to about 60 weight percent, about 25 to about 50 weight percent, about 25 to about 45 weight percent, about 25 to about 40 weight percent, about 25 to about 35 weight percent, about 25 to about 30 weight percent, about 30 to about 70 weight percent, about 30 to about 60 weight percent, about 30 to about 50 weight percent, about 30 to about 45 weight percent, about 30 to about 40 weight percent, or about 30 to about 35 weight percent, based on the total weight of the stream in line 140.

In some embodiments, the molar ratio of formamide (or other carboxylic acid amide such as N-methylformamide) to N-vinylformamide (or other N-vinyl carboxylic acid amide such as N-methyl,N-vinylformamide) in the stream in line 140 can be at least about 0.3:1, at least about 0.5:1, at least about 0.75:1, at least about 1:1, at least about 1.05:1, at least about 1.1:1, at least about 1.15:1, at least about 1.2:1, at least about 1.3, or at least about 1.5 and/or not more than about 3:1, not more than about 2.5:1, not more than about 2:1, not more than about 1.75:1, or it can be in the range of from about 0.3:1 to about 3:1, about 0.3:1 to about 2.5:1, about 0.3:1 to about 2:1, about 0.3:1 to about 1.75:1, about 0.5:1 to about 3:1, about 0.5:1 to about 2.5:1, about 0.5:1 to about 2:1, about 0.5:1 to about 1.75:1, about 0.75:1 to about 3:1, about 0.75:1 to about 2.5:1, about 0.75:1 to about 2:1, about 0.75:1 to about 1.75:1, about 1:1 to about 3:1, about 1:1 to about 2.5:1, about 1:1 to about 2:1, about 1:1 to about 1.75:1, about 1.05:1 to about 3:1, about 1.05:1 to about 2.5:1, about 1.05:1 to about 2:1, about 1.05:1 to about 1.75:1, about 1.1:1 to about 3:1, about 1.1:1 to about 2.5:1, about 1.1:1 to about 2:1, about 1.1:1 to about 1.75:1, about 1.15:1 to about 3:1, about 1.15:1 to about 2.5:1, about 1.15:1 to about 2:1, about 1.15:1 to about 1.75:1, about 1.2:1 to about 3:1, about 1.2:1 to about 2.5:1, about 1.2:1 to about 2:1, about 1.2:1 to about 1.75:1, about 1.3:1 to about 3:1, about 1.3:1 to about 2.5:1, about 1.3:1 to about 2:1, about 1.3:1 to about 1.75:1, about 1.5:1 to about 3:1, about 1.5:1 to about 2.5:1, about 1.5:1 to about 2:1, or about 1.5:1 to about 1.75:1.

Additionally, the crude product stream in line 140 may include at least one alcohol. For example, in some embodiments, the crude product stream in line 140 may comprise at least about 5, at least about 10, at least about 15, or at least about 20 weight percent and/or not more than about 50, not more than about 45, not more than about 40, or not more than about 35 weight percent of an alcohol, or the amount of alcohol in the stream in line 140 can be in the range of from about 5 to about 50 weight percent, about 5 to about 45 weight percent, about 5 to about 40 weight percent, about 5 to about 35 weight percent, about 10 to about 50 weight percent, about 10 to about 45 weight percent, about 10 to about 40 weight percent, about 10 to about 35 weight percent, about 5 to about 50 weight percent, about 15 to about 45 weight percent, about 15 to about 40 weight percent, about 15 to about 35 weight percent, about 20 to about 50 weight percent, about 20 to about 45 weight percent, about 20 to about 40 weight percent, or about 20 to about 35 weight percent, based on the total weight of the stream in line 140.

As shown in FIG. 1, the crude product stream withdrawn from pyrolysis zone 50 in line 140 can be routed to a final separation zone 60. In some embodiments, final separation zone 60 can include an alcohol flash column 62 and an N-vinylformamide purification column 64. Although shown in FIG. 1 as including only two columns, any suitable number of columns or other separation devices could be used to achieve the desired recovery of N-vinylformamide (or other N-vinyl carboxylic acid amide such as N-methyl,N-vinylformamide) from the crude product stream in line 140. In some embodiments, final separation zone 60 may be configured to recover at least about 60, at least about 65, at least about 70, at least about 75, at least about 80, at least about 85, at least about 90, at least about 92, at least about 95, or at least about 99 percent of the total amount of N-vinylformamide (or other N-vinyl carboxylic acid amide such as N-methyl,N-vinylformamide) introduced into final separation zone 60 in line 140. In some embodiments, the concentration of N-vinylformamide in the final product stream withdrawn from final separation zone 60 in line 146 can be at least about 60, at least about 70, at least about 75, at least about 80, at least about 85, at least about 90, at least about 95, or at least about 99 weight percent, based on the total weight of the stream in line 146.

As shown in FIG. 1, the crude product stream withdrawn from pyrolysis zone 50 in line 140 may be introduced into alcohol flash column 62, wherein it can be separated into an overhead stream enriched in alcohol in line 142 and a bottoms stream enriched in N-vinylformamide (or other N-vinyl carboxylic amide such as N-methyl,N-vinylformamide) and formamide (or other carboxylic acid amide such as N-methylformamide) in line 144. In some embodiments, the overhead stream in line 142 can include at least about 50, at least about 55, at least about 60, at least about 65, at least about 70, at least about 75, at least about 80, at least about 85, at least about 90, or at least about 95 percent of the total alcohol introduced into alcohol flash column 62 in line 140.

The overhead stream from alcohol flash column 62 in line 142 may include at least about 60, at least about 65, at least about 70, at least about 75, at least about 80, at least about 85, at least about 90, or at least about 95 weight percent alcohol, based on the total weight of the stream in line 142. Small amounts of other components, including, for example, formamide (or other carboxylic acid amide such as N-methylformamide) or N-vinylformamide (or other N-vinyl carboxylic acid amide such as N-methyl,N-vinylformamide) may also be present, in addition to trace amounts of other components including, various impurities, residual catalyst, and/or solvent. In some embodiments, the stream in line 142 can include not more than about 5, not more than about 3, not more than about 2, not more than about 1, not more than about 0.5 weight percent of components other than the alcohol, based on the total weight of the stream in line 142.

As shown in FIG. 1, the overhead stream withdrawn from alcohol flash column 62 may be routed to alcohol recycle and recovery zone 72. As discussed previously, the stream in line 142 may be combined prior to, or within, alcohol recycle and recovery zone 72 with the alcohol recovered from alcohol distillation column 44 in line 126, and the combined stream may be further processed prior to being reused in second reaction zone 30. In some embodiments, at least about 50, at least about 60, at least about 70, at least about 80, at least about 90, or at least about 95 percent of the stream in lines 142 and/or 126 may be routed to alcohol recycle and recovery zone 72, so that at least about 20, at least about 30, at least about 40, at least about 50, at least about 60 and/or not more than about 90, not more than about 80, not more than about 70 weight percent of the total amount of the alcohol introduced into second reaction zone 30 may be recycled.

In some embodiments, the amount of recycled alcohol utilized in second reaction zone 30 can be in the range of from about 20 to about 90 weight percent, about 20 to about 80 weight percent, about 20 to about 70 weight percent, about 30 to about 90 weight percent, about 30 to about 80 weight percent, about 30 to about 70 weight percent, about 40 to about 90 weight percent, about 40 to about 80 weight percent, about 40 to about 70 weight percent, about 50 to about 90 weight percent, about 50 to about 80 weight percent, about 50 to about 70 weight percent, about 60 to about 90 weight percent, about 60 to about 80 weight percent, or about 60 to about 70 weight percent, based on the total weight of alcohol introduced into second separation zone 30.

The bottoms stream withdrawn from alcohol flash column 62 in line 144 may be enriched in N-vinylformamide (or other N-vinyl carboxylic acid amide such as N-methyl,N-vinylformamide). For example, in some embodiments, the stream in line 144 may include at least about 50, at least about 55, at least about 60, at least about 65, at least about 70, at least about 75, at least about 80, at least about 85, at least about 90, or at least about 95 percent of the total amount of N-vinylformamide introduced into alcohol flash column 62 in line 140. In some embodiments, the stream in line 144 can include at least about 20, at least about 30, at least about 35, at least about 40, at least about 50, at least about 55 weight percent and/or not more than about 90, not more than about 85, not more than about 80, or not more than about 75 weight percent of N-vinylformamide, based on the total weight of the stream. The total amount of N-vinylformamide in the stream in line 144 can be in the range of from about 20 to about 90 weight percent, about 20 to about 85 weight percent, about 20 to about 80 weight percent, about 20 to about 75 weight percent, about 30 to about 90 weight percent, about 30 to about 85 weight percent, about 30 to about 80 weight percent, about 30 to about 75 weight percent, about 35 to about 90 weight percent, about 35 to about 85 weight percent, about 35 to about 80 weight percent, about 35 to about 75 weight percent, about 40 to about 90 weight percent, about 40 to about 85 weight percent, about 40 to about 80 weight percent, about 40 to about 75 weight percent, about 50 to about 90 weight percent, about 50 to about 85 weight percent, about 50 to about 80 weight percent, about 50 to about 75 weight percent, about 55 to about 90 weight percent, about 55 to about 85 weight percent, about 55 to about 80 weight percent, or about 55 to about 75 weight percent, based on the total weight of the stream in line 144.

The bottoms stream withdrawn from alcohol flash column 62 in line 144 may also include an excess of formamide (or other carboxylic acid amide such as N-methylformamide). In some embodiments, the stream in line 144 may also include an excess of formamide. For example, the stream in line 144 may comprise at least about 1, at least about 2, at least about 5, at least about 10, at least about 15, at least about 20, at least about 25, at least about 30 weight percent and/or not more than about 70, not more than about 60, not more than about 50, not more than about 45, not more than about 40, not more than about 35, not more than about 30, or not more than about 25 weight percent formamide (or other carboxylic acid amide such as N-methylformamide), based on the total weight of the stream in line 144. This is in contrast to many conventional processes, which would include only trace amounts of formamide, if any, in the bottoms stream withdrawn from alcohol flash column 62 in line 144.

The total amount of formamide in the bottoms stream withdrawn from alcohol flash column 62 in line 144 can be in the range of from about 1 to about 70 weight percent, about 1 to about 60 weight percent, about 1 to about 50 weight percent, about 1 to about 45 weight percent, about 1 to about 40 weight percent, about 1 to about 35 weight percent, about 1 to about 30 weight percent, about 1 to about 25 weight percent, about 2 to about 70 weight percent, about 2 to about 60 weight percent, about 2 to about 50 weight percent, about 2 to about 45 weight percent, about 2 to about 40 weight percent, about 2 to about 35 weight percent, about 2 to about 30 weight percent, about 2 to about 25 weight percent, about 5 to about 70 weight percent, about 5 to about 60 weight percent, about 5 to about 50 weight percent, about 5 to about 45 weight percent, about 5 to about 40 weight percent, about 5 to about 35 weight percent, about 5 to about 30 weight percent, about 5 to about 25 weight percent, about 10 to about 70 weight percent, about 10 to about 60 weight percent, about 10 to about 50 weight percent, about 10 to about 45 weight percent, about 10 to about 40 weight percent, about 10 to about 35 weight percent, about 10 to about 30 weight percent, about 10 to about 25 weight percent, about 15 to about 70 weight percent, about 15 to about 60 weight percent, about 15 to about 50 weight percent, about 15 to about 45 weight percent, about 15 to about 40 weight percent, about 15 to about 35 weight percent, about 15 to about 30 weight percent, about 15 to about 25 weight percent, about 20 to about 70 weight percent, about 20 to about 60 weight percent, about 20 to about 50 weight percent, about 20 to about 45 weight percent, about 20 to about 40 weight percent, about 20 to about 35 weight percent, about 20 to about 30 weight percent, about 20 to about 25 weight percent, about 25 to about 70 weight percent, about 25 to about 60 weight percent, about 25 to about 50 weight percent, about 25 to about 45 weight percent, about 25 to about 70 weight percent, about 25 to about 60 weight percent, about 25 to about 50 weight percent, about 25 to about 40 weight percent, about 25 to about 35 weight percent, about 25 to about 30 weight percent, about 30 to about 70 weight percent, about 30 to about 60 weight percent, about 30 to about 50 weight percent, about 30 to about 45 weight percent, about 30 to about 40 weight percent, or about 30 to about 35 weight percent, based on the total weight of the stream in line 144.

In some embodiments, the molar ratio of formamide (or other carboxylic acid amide such as N-methylformamide) to N-vinylformamide (or other N-vinyl carboxylic acid amide such as N-methyl,N-vinylformamide) in the stream in line 144 can be at least about 0.3:1, at least about 0.5:1, at least about 0.75:1, at least about 1:1, at least about 1.05:1, at least about 1.1:1, at least about 1.15:1, at least about 1.2:1, at least about 1.3, or at least about 1.5 and/or not more than about 3:1, not more than about 2.5:1, not more than about 2:1, not more than about 1.75:1, or it can be in the range of from about 0.3:1 to about 3:1, about 0.3:1 to about 2.5:1, about 0.3:1 to about 2:1, about 0.3:1 to about 1.75:1, about 0.5:1 to about 3:1, about 0.5:1 to about 2.5:1, about 0.5:1 to about 2:1, about 0.5:1 to about 1.75:1, about 0.75:1 to about 3:1, about 0.75:1 to about 2.5:1, about 0.75:1 to about 2:1, about 0.75:1 to about 1.75:1, about 1:1 to about 3:1, about 1:1 to about 2.5:1, about 1:1 to about 2:1, about 1:1 to about 1.75:1, about 1.05:1 to about 3:1, about 1.05:1 to about 2.5:1, about 1.05:1 to about 2:1, about 1.05:1 to about 1.75:1, about 1.1:1 to about 3:1, about 1.1:1 to about 2.5:1, about 1.1:1 to about 2:1, about 1.1:1 to about 1.75:1, about 1.15:1 to about 3:1, about 1.15:1 to about 2.5:1, about 1.15:1 to about 2:1, about 1.15:1 to about 1.75:1, about 1.2:1 to about 3:1, about 1.2:1 to about 2.5:1, about 1.2:1 to about 2:1, about 1.2:1 to about 1.75:1, about 1.3:1 to about 3:1, about 1.3:1 to about 2.5:1, about 1.3:1 to about 2:1, about 1.3:1 to about 1.75:1, about 1.5:1 to about 3:1, about 1.5:1 to about 2.5:1, about 1.5:1 to about 2:1, or about 1.5:1 to about 1.75:1.

As shown in FIG. 1, the bottoms steam in line 144 can be introduced into an N-vinylformamide purification column 64, wherein it may be separated into an N-vinylformamide-enriched overhead product stream in line 146 and a bottoms product stream enriched in formamide. In some embodiments, N-vinylformamide purification column 64 may be configured so that at least about 50, at least about 55, at least about 60, at least about 65, at least about 70, at least about 75, at least about 80, at least about 85, at least about 90, or at least about 95 percent of the total weight of N-vinylformamide introduced into N-vinylformamide purification column 64 in line 144 is recovered in the overhead product stream in line 146. In some embodiments, the stream in line 146 can include at least about 70, at least about 75, at least about 80, at least about 85, at least about 90, at least about 95 weight percent N-vinylformamide (or other N-vinyl carboxylic acid amide such as N-methyl,N-vinylformamide), based on the total weight of the stream.

The bottoms stream withdrawn from the N-vinylformamide purification column 64 in line 148 can include formamide (or other carboxylic acid amide such as N-methylformamide), along with trace amounts of other components. In some embodiments, at least a portion of the formamide introduced into N-vinylformamide purification column 64 in line 144 may remain within the column 64 and, in particular, within lower portion of the column including, for example, its reboiler circuit. Although not wishing to be bound by theory, it is hypothesized that maintaining at least a portion of the formamide within the column and, in particular, in the lower portion of the column, may help minimize decomposition of the N-vinylformamide product. In some embodiments, at least about 1, at least about 2, at least about 3 percent and/or not more than about 10, not more than about 8, not more than about 5 percent of the total amount N-vinylformamide introduced into N-vinylformamide purification column 64 may be retained within the column, or the amount retained can be in the range of from about 1 to about 10 percent, about 1 to about 8 percent, about 1 to about 5 percent, about 2 to about 10 percent, about 2 to about 8 percent, about 2 to about 5 percent, about 3 to about 10 percent, about 3 to about 8 percent, or about 3 to about 5 percent, based on the total amount of N-vinylformamide introduced in line 144. As a result, in some embodiments, the bottoms stream withdrawn from N-vinylformamide purification column 64 may include not more than about 10, not more than about 5, not more than about 3, not more than about 2, or not more than about 1 weight percent of the byproducts of N-vinylformamide decomposition.

In some embodiments, the stream in line 148 can comprise formamide (or other carboxylic acid amide such as N-methylformamide) in an amount of at least about 30, at least about 40, at least about 50, or at least about 60 weight percent and/or not more than about 90 weight percent, not more than about 80 weight percent, or not more than about 75 weight percent, based on the total weight of the stream in line 148, or the formamide (or other carboxylic acid amide such as N-methylformamide) may be present in an amount in the range of from about 30 to about 90 weight percent, about 30 to about 80 weight percent, about 30 to about 75 weight percent, about 40 to about 90 weight percent, about 40 to about 80 weight percent, about 40 to about 75 weight percent, about 50 to about 90 weight percent, about 50 to about 80 weight percent, about 50 to about 75 weight percent, about 60 to about 90 weight percent, about 60 to about 80 weight percent, or about 60 to about 75 weight percent, based on the total weight of the stream in line 148.

As shown in FIG. 1, at least a portion of the stream withdrawn from N-vinylformamide purification column 64 in line 148 can be routed to a formamide recycle and recovery zone 74, wherein the stream can be further processed for subsequent recycle to first reaction zone 20. In some embodiments, at least about 50, at least about 60, at least about 70, at least about 80, at least about 90, or at least about 95 percent of the stream in line 148 may be routed to formamide recycle and recovery zone 74, so that at least about 20, at least about 30, at least about 40, at least about 50, at least about 60 and/or not more than about 90, not more than about 80, not more than about 70 weight percent of the total amount of formamide introduced into first reaction zone 20 can be recycled.

In some embodiments, the amount of recycled formamide utilized in first reaction zone 20 can be in the range of from about 20 to about 90 weight percent, about 20 to about 80 weight percent, about 20 to about 70 weight percent, about 30 to about 90 weight percent, about 30 to about 80 weight percent, about 30 to about 70 weight percent, about 40 to about 90 weight percent, about 40 to about 80 weight percent, about 40 to about 70 weight percent, about 50 to about 90 weight percent, about 50 to about 80 weight percent, about 50 to about 70 weight percent, about 60 to about 90 weight percent, about 60 to about 80 weight percent, or about 60 to about 70 weight percent, based on the total weight of formamide introduced into first reaction zone 20.

The following examples are given to illustrate the invention and to enable any person skilled in the art to make and use the invention. It should be understood, however, that the invention is not to be limited to the specific conditions or details described in these examples. The patentable scope of the invention is defined by the claims, and may include other examples that occur to those skilled in the art.

EXAMPLES

Example 1

Several reactions for producing 1-hydroxyethylformamide were conducted by reacting formamide and acetaldehyde in the presence of a solvent and a basic catalyst in a lab-scale batch reactor. All reactions were carried out at a temperature of 25° C. for 2 hours. Several different solvents, including methanol (MeOH), isopropanol (IPA), and 2-ethylhexanol (2EH), were used, along with several different catalysts, including trimethylamine (TEA), N,N-dimethylisopropylamine (DMIPA), N,N-diisopropyl ethanolamine (DIPEA), potassium bicarbonate (KHCO3), and 8-diazabicyclo[5.4.0]undec-7-ene (DBU), to determine the effect of solvent and/or type of catalyst on the yield of 1-hydroxyethylformamide. Additionally, the amount of catalyst, amount of solvent, and ratio of formamide to acetaldehyde (mol/mol) were also varied. The results of each of these reactions is summarized in Table 1, below.

TABLE 1

Yields for Various Synthesis Reactions of 1-hydroxyethylformamide

| Reaction | Formamide/Acetaldehyde Ratio (mol/mol) | Solvent Type | Solvent Amount (wt %) | Catalyst Type | Catalyst Amount (wt %) | Yield (%) |
|---|---|---|---|---|---|---|
| R-1 | 0.8:1 | MeOH | 50 | TEA | 0.85 | 47 |
| R-2 | 0.8:1 | MeOH | 50 | DBU | 0.85 | 49 |
| R-3 | 0.8:1 | MeOH | 50 | KHCO3 | 0.85 | 4 |
| R-4 | 0.8:1 | MeOH | 50 | DBU | 0.80 | 47 |
| R-5 | 0.8:1 | MeOH | 50 | DBU | 1.50 | 48 |
| R-6 | 0.8:1 | MeOH | 30 | DBU | 0.85 | 60 |
| R-7 | 0.8:1 | MeOH | 50 | DBU | 0.85 | 48 |
| R-8 | 0.8:1 | MeOH | 70 | DBU | 0.85 | 18 |
| R-9 | 0.6:1 | MeOH | 50 | DBU | 0.85 | 55 |
| R-10 | 0.8:1 | IPA | 50 | TEA | 0.85 | 32 |
| R-11 | 0.8:1 | IPA | 50 | DBU | 0.85 | 79 |
| R-12 | 0.8:1 | IPA | 70 | DBU | 0.85 | 64 |
| R-13 | 0.8:1 | IPA | 50 | DBU | 0.40 | 12 |
| R-14 | 0.8:1 | IPA | 50 | DBU | 0.80 | 79 |
| R-15 | 0.8:1 | IPA | 50 | DBU | 1.20 | 10 |
| R-16 | 0.8:1 | 2EH | 50 | DBU | 0.80 | 86 |
| R-17 | 1.38:1 | 2EH | 50 | DBU | 0.80 | 89 |
| R-18 | 1.38:1 | MeOH | 50 | DBU | 0.85 | 56 |
| R-19 | 1.5:1 | H2O | 50 | TEA | 0.85 | 95 |
| R-20 | 1.8:1 | — | — | TEA | 0.85 | 96 |
| R-21 | 2.0:1 | — | — | TEA | 0.85 | 98 |
| R-22 | 2.5:1 | — | — | TEA | 0.85 | 99 |
| R-23 | 2.0:1 | MeOH | 50 | DBU | 0.85 | 96 |
| R-24 | 2.0:1 | MeOH | 50 | TEA | 0.85 | 95 |
| R-25 | 2.0:1 | EtOH | 50 | TEA | 0.85 | 99 |
| R-26 | 2.0:1 | — | — | DMIPA | 0.85 | 99 |
| R-27 | 2.0:1 | — | — | DIPEA | 0.85 | 98 |

As shown in Table 1, above, the type of catalyst used may impact the final yield of 1-hydroxyethylformamide. For example, as shown by comparison of the results of reactions R-1 through R-3 above, when methanol is used as a solvent, both TEA and DBU provide yields of 47 percent and 49 percent respectively, while KHCO3 produces only a 4 percent yield of 1-hydroxyethylformamide. Similarly, as shown by comparing the results of reactions R-10 and R-11, when isopropanol is used as a solvent, use of TEA as a catalyst provides a 32 percent yield, while DBU catalyst results in a 1-hydroxyethylformamide yield of 79 percent. Additionally, as shown by comparing the results of reactions R-1 with R-10, which both use 0.85 weight percent TEA but different solvents, and reactions R-2 with R-11, which both use 0.85 weight percent DBU but different solvents, it can also be seen that the type of solvent may also impact the yield achieved by a given catalyst.

As shown by the comparison of the results of reactions R-4 and R-5, when methanol is used as the solvent, the amount of catalyst has a minimal influence on the yield. However, as shown by comparison of the results of reactions R-13 through R-15, when isopropanol is used as the solvent, the amount of catalyst has a greater impact on the final product yield. For example, it appears that utilizing less DBU catalyst (e.g., 0.4 wt % in R-13) likely causes the reaction to proceed too slowly, while more DBU catalyst (e.g., 1.2 wt % in R-15) causes the acetaldehyde to polymerize, which also lowers yield. Therefore, as shown in Table 1, above, of the amounts tested, 0.80 weight percent in R-14 is the optimal amount of DBU catalyst to employ when reacting formamide and acetaldehyde in an isopropanol solvent among the reactions performed above.

As shown by comparison of the results of reactions R-6 through R-8 and the comparison of the results of reactions R-11 and R-12, for a given solvent, the amount of solvent used during the reaction may also impact the final yield of 1-hydroxyethylformamide. In general, more solvent tends to result in less yield. Further, as shown by comparison of the results of reactions R-7 and R-8 with the results of reactions R-11 and R-12, this impact appears to be more pronounced when methanol is used as a solvent, as compared to isopropanol. Similarly, it can be seen from comparison of the results of reactions R-7 and R-9 that use of a larger excess of acetaldehyde (i.e., a lower formamide-to-acetaldehyde ratio) can also lead to higher yields, when methanol is used as the solvent.

Further, as shown by comparison of the results of reactions R-19 through R-21, higher formamide-to-acetaldehyde ratios and, in particular, those above 1.5:1, result in higher yields closer to about 100 percent. Additionally, when higher amounts of formamide are present, the impact of the type of solvent and type of catalyst on the overall yield becomes smaller.

Example 2

Several reactions were performed by reacting formamide and acetaldehyde to form 1-hydroxyethylformamide in the presence of a solvent and 8-diazabicyclo[5.4.0]undec-7-ene (DBU) catalyst. The reactions were performed in a continuous, plug flow reaction system that included separate reagent vials to control the amount of each reagent added. One vial included a solution of formamide, half of the total amount of solvent used, and the catalyst, while the other vial included a solution of acetaldehyde and the remaining amount of solvent. The solution from each vial was pumped into the system using separate reaction pumps via separate lines of ⅛-inch diameter tubing before being combined in a single reaction line and introduced into a heating element, which was used to control the reaction temperature. A backpressure valve was used to maintain the reaction pressure at 10 bar gauge or below so that the reactants were maintained in the liquid phase. The reaction product was collected in a separate reaction vial. Several reactions were performed using this system by varying several parameters, as discussed below.

An initial reaction was performed using the reaction apparatus described above at a temperature of 20° C. and a residence time of 15 minutes. The molar ratio of formamide-to-acetaldehyde was 0.83:1 and isopropanol was used as a solvent in an amount of 45 weight percent, based on the total weight of the initial reaction mixture. The reaction was performed using DBU as the catalyst in an amount of 1 weight percent, based on the total weight of the initial reaction mixture. The resulting reaction product was analyzed by HPLC using an Agilent LC 1260 HPLC with a 1290 DAD. The reaction product was passed through a Zorbax® SB-C18 column with dimension of 150 mm×4.6 mm×3.5 µm at a column temperature of 35° C. The injector volume was 2 µL and the mobile phase included water and acetonitrile at a flow of 0.5 mL/min. The resulting product included 33.4 weight percent 1-hydroxyethylformamide and 10.23 weight percent formamide for a 1-hydroxyethylformamide yield of 68 percent.

A second, similar reaction was performed, but with 56 weight percent isopropanol as the solvent, based on the total weight of the initial reaction mixture. The resulting reaction product was analyzed by HPLC according to the method described above and included 26.14 weight percent 1-hydroxyethylformamide and 5.96 weight percent formamide. However, the 1-hydroxyethylformamide yield was 67.4 percent, which was slightly less than the 68 percent yield achieved by the previously-discussed reaction. It was concluded that because of the low solubility of 1-hydroxyethylformamide in isopropanol (20.1 weight percent, measured as described above), higher amounts of isopropanol results in lower concentrations of reagents and, as a result, products in solution.

Example 3

Figure 2:
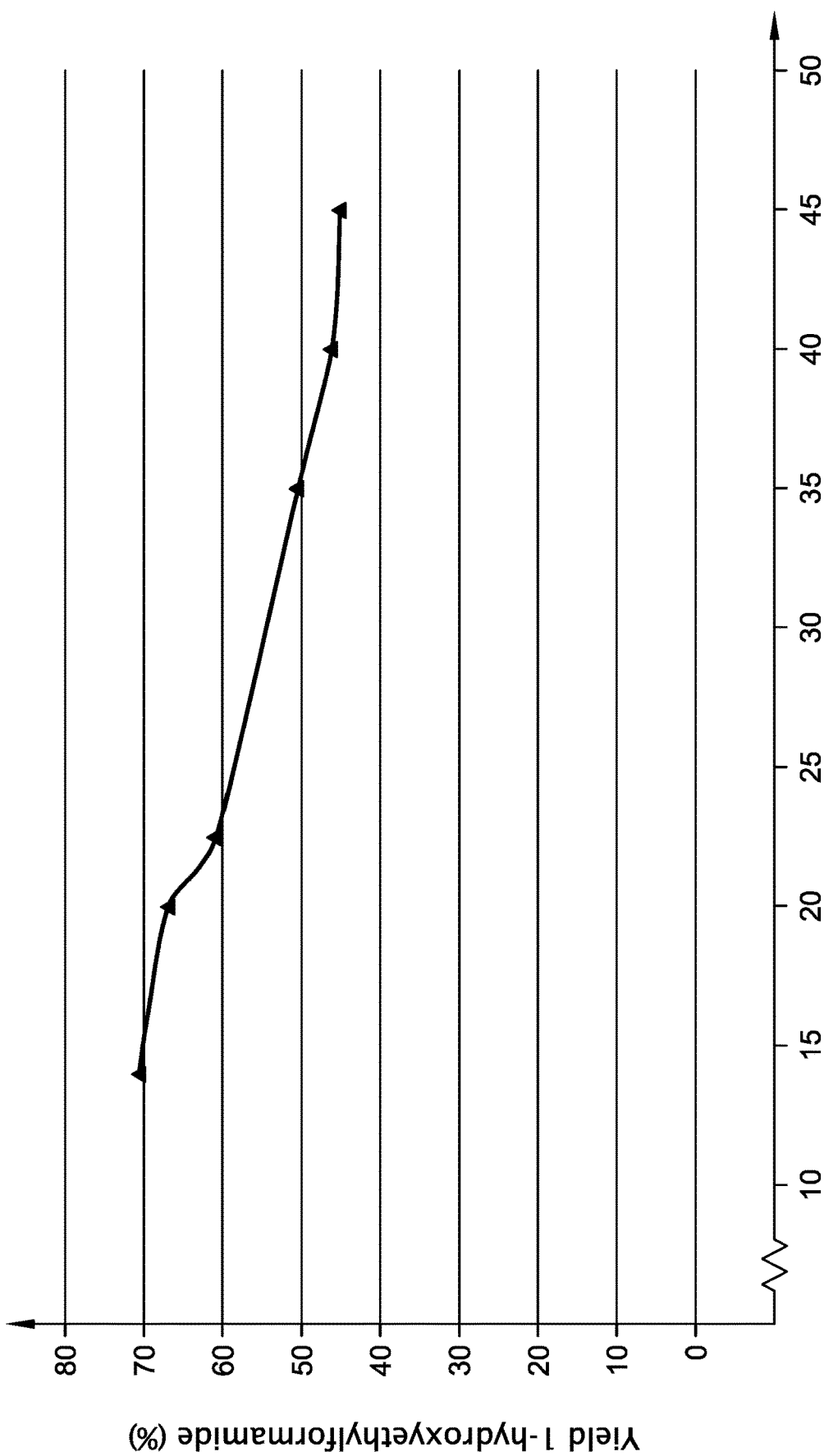
FIG. 2 is a graph illustrating the relationship between reaction temperature and yield of 1-hydroxyethylformamide in several reactions performed as described in Example 3.

Several reactions were performed in a similar manner as described in Example 2 above, but at various reaction temperatures between 15° C. and 45° C. Additionally, the isopropanol concentration used was 35 weight percent, based on the total weight of the initial reaction medium. The results of these reactions are summarized graphically in FIG. 2, which shows the yield of 1-hydroxyethylformamide as a function of reaction temperature over the above range. As shown in FIG. 2, reaction temperature and 1-hydroxyethylformamide yield are inversely proportional over the temperature range shown, with lower temperatures resulting in higher 1-hydroxyethylformamide yields and higher temperatures resulting in lower yields of 1-hydroxyethylformamide.

Example 4

Another set of reactions was performed using various ratios of formamide-to-acetaldehyde. These reactions were performed in a similar manner as Example 2, above, but with hexanol as the solvent. The results of these reactions are provided in Table 2, below.

TABLE 2

Results of Further Reactions with Various Formamide-to-Acetaldehyde ratios

| Formamide/Acetaldehyde Ratio (mol/mol) | Yield (%) |
|---|---|
| 0.82:1 | 64.03 |
| 0.99:1 | 57.26 |

TABLE 2-continued

Results of Further Reactions with Various Formamide-to-Acetaldehyde ratios

| Formamide/Acetaldehyde Ratio (mol/mol) | Yield (%) |
|---|---|
| 1.09:1 | 60.40 |
| 1.19:1 | 61.60 |
| 1.39:1 | 68.90 |
| 1.6:1 | 75.9 |
| 2.5:1 | 95.0 |

Figure 3:
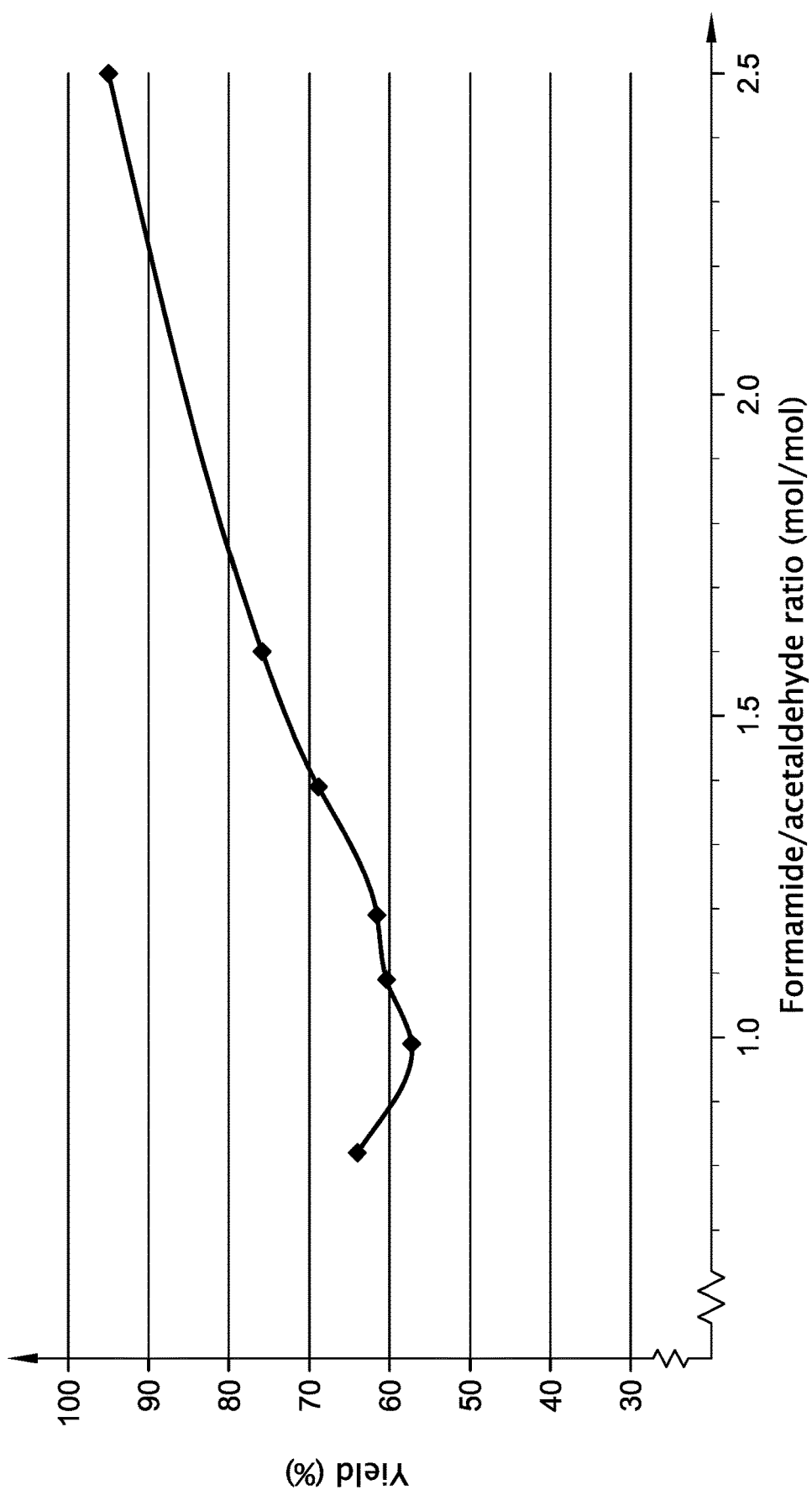
FIG. 3 is a graph illustrating the relationship between the formamide-to-acetaldehyde molar ratio and yield of 1-hydroxyethylformamide in several reactions performed as described in Example 4.
Figure 4:
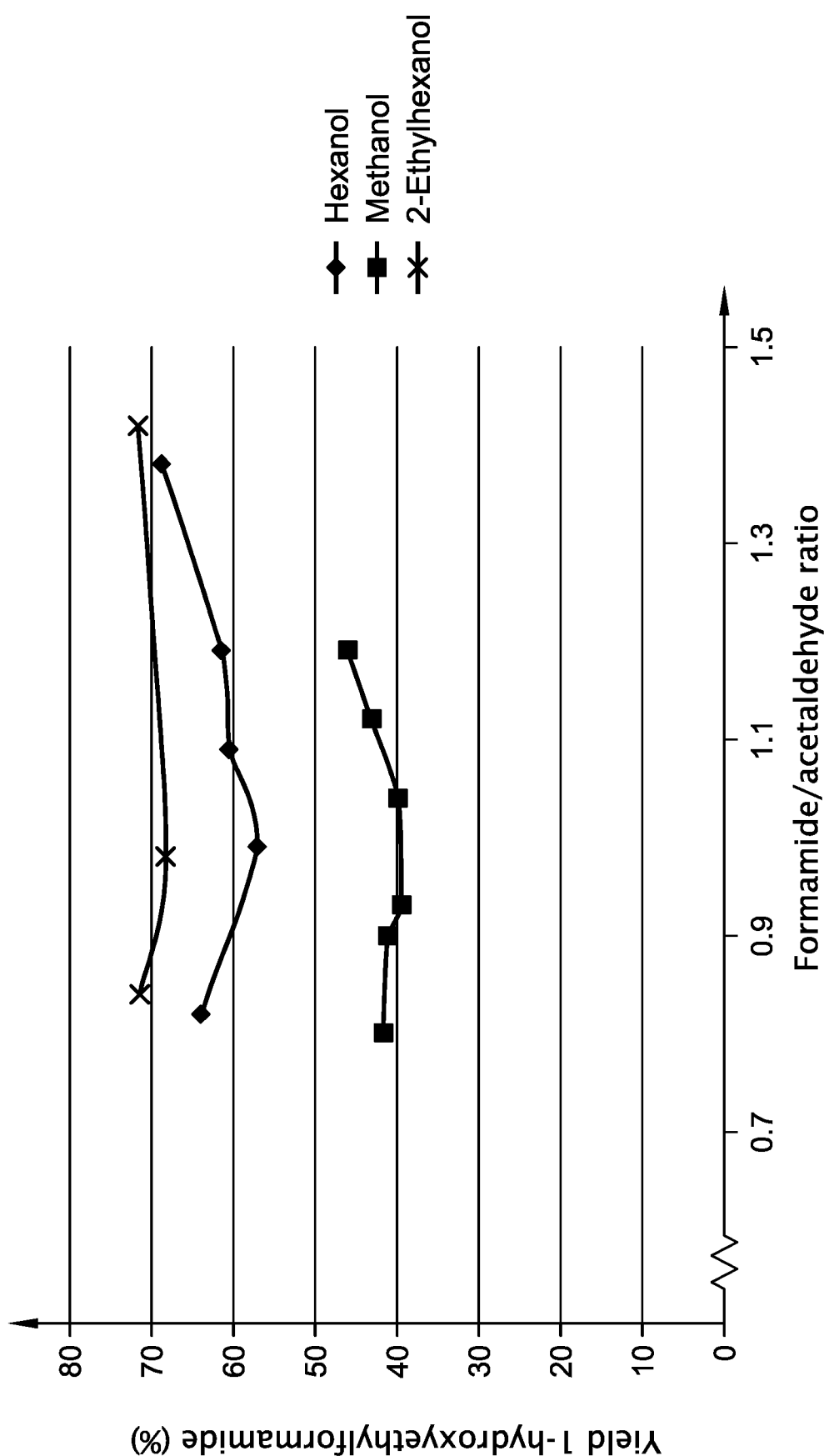
FIG. 4 is a graph illustrating the relationship between the formamide-to-acetaldehyde molar ratio and yield of 1-hydroxyethylformamide for various solvents in several reactions performed as described in Example 4.

Additionally, the results are summarized graphically in FIG. 3, which shows the yield of 1-hydroxyethylformamide as a function of the formamide-to-acetaldehyde ratio. As shown in FIG. 3, formamide-to-acetaldehyde ratios greater than or less than 1 (i.e., non-equimolar amounts) result in higher yield of 1-hydroxyethylformamide. Use of acetaldehyde in excess (i.e., formamide to acetaldehyde ratios less than 1:1) is undesirable because the subsequent addition of sulfuric acid during alkoxylation results in a side reaction between the solvent and excess acetaldehyde to form an acetal byproduct. Thus, higher yields are desirably achieved with an excess of formamide (i.e., formamide to acetaldehyde ratios greater than 1:1).

Two additional sets of reactions were performed as described above with varying formamide-to-acetaldehyde ratios, but with methanol and 2-ethylhexanol as the solvent. The results of these reactions are summarized in FIG. 5, which shows the yield of 1-hydroxyethylformamide as a function of formamide-to-acetaldehyde ratio when hexanol, methanol, and 2-ethylhexanol are used as solvents. As shown in FIG. 5, the type of solvent also impacts the yield of 1-hydroxyethylformamide, which ranges from less than 50 percent when methanol is used as the solvent to more than 70 percent when the solvent is 2-ethylhexanol.

Example 5

Another set of reactions was performed using various ratios of formamide-to-acetaldehyde. These reactions were performed in a similar manner as Example 2, above, but with ethanol as solvent and triethylamine as the catalyst. The results of these reactions are provided in Table 3, below.

TABLE 3

Results of Further Reactions with Various Formamide-to-Acetaldehyde ratios

| Formamide/Acetaldehyde Ratio (mol/mol) | Yield (%) |
|---|---|
| 0.82:1 | 59 |
| 0.99:1 | 49 |
| 1.09:1 | 52 |
| 1.19:1 | 56 |
| 1.39:1 | 60 |
| 1.6:1 | 79 |
| 2.0:1 | 99 |
| 2.5:1 | 99 |

Another set of reactions was performed using various ratios of formamide-to-acetaldehyde. These reactions were performed in a similar manner as Example 2, above, but with water as solvent and triethylamine as the catalyst. The results of these reactions are provided in Table 4, below.

TABLE 4

Results of Further Reactions with Various Formamide-to-Acetaldehyde ratios

| Formamide/Acetaldehyde Ratio (mol/mol) | Yield (%) |
|---|---|
| 1.1, 1 | 97 |
| 1.25:1 | 99 |
| 1.5:1 | 99 |

Example 7

Another reaction was performed in a similar manner as described in Example 2, above, but in the absence of a solvent. Instead, an excess of formamide was used. The solubility of 1-hydroxyethylformamide in formamide is about 60 weight percent, so formamide, in excess, may also act as a solvent during the formation of 1-hydroxyethylformamide. The molar ratio of formamide-to-acetaldehyde was 2.5:1. The reaction was performed on the apparatus described in Example 2 at a temperature of 20° C. and a residence time of 15 minutes. An amount of 1 weight percent DBU was used as the catalyst and no additional solvent was employed. The reaction product obtained was analyzed by HPLC and included 46.9 weight percent formamide and 52.4 weight percent 1-hydroxyethylformamide, which corresponded to a yield of 99.9 percent.

Several additional reactions were carried out in a similar manner, but with varying residence times and with different types of catalyst. The results of these experiments are summarized in Table 5, below.

TABLE 5

Yield for Reactions with Varying Catalyst Types and Residence Time (No Solvent)

| Catalyst Type | Residence Time (min) | Formamide (wt %) | 1-hydroxyethylformamide (wt %) | Yield (%) |
|---|---|---|---|---|
| DBU | 15 | 46.90 | 52.40 | 99.9 |
| TMG | 15 | 47.91 | 50.59 | 98.9 |
| TEA | 15 | 48.81 | 52.89 | 99.9 |
| TEA | 7 | 48.50 | 52.20 | 99.7 |

As shown in Table 5, the performance of each of the three types of catalyst tested—DBU, TEA, and 1,1,3,3-tetramethylguanidine (TMG)—were nearly equivalent and resulted in nearly 100 percent yield. Further, as shown in Table 5, reactions carried out in the presence of excess formamide and no additional solvent exhibited short residence times, achieving nearly 100 percent conversion in residence times as short as 7 minutes.

Example 8

Another 1-hydroxyethylformamide synthesis reaction was performed by reacting 2.5 molar equivalents of formamide with 1 molar equivalent of acetaldehyde in the presence of 1 weight percent of triethylamine as a catalyst. No additional solvent was used. The reaction was performed in a continuous, plug flow reaction system as described in Example 2, above. The product included 41.6 weight percent formamide and 58.4 weight percent 1-hydroxyethylformamide, which equated to a 1-hydroxyethylformamide yield of 98 percent.

Next, 2.1 molar equivalents of ethanol (based on the amount of 1-hydroxyethylformamide) were added to this reaction mixture together with 0.7 weight percent sulfuric acid, based on the total reaction mixture, and a batch reaction was performed at 35° C. for 30 minutes. The resulting reaction mixture included 20.6 weight percent ethanol, 22.7 weight percent formamide, 47.9 weight percent 1-ethoxyethylformamide, and 7.4 weight percent water for a 1-ethoxyethylformamide yield of 94 percent.

This stream was then introduced into a continuous whipped film evaporator at a temperature of 105° C. and a vacuum pressure of 57 mbara. The resulting bottom stream, which included 65 percent of the total amount introduced into the evaporator, and a distillate stream, which included 35 percent of the total amount introduced into the evaporator, were withdrawn from the evaporator. The bottom stream included 1.7 weight percent ethanol, 36.9 weight percent formamide, and 57.3 weight percent 1-ethoxyethylformamide, along with other minor impurities. The distillate stream included 87 weight percent ethanol, 3 weight percent formamide, 0.91 weight percent triethylamine and 9 weight percent water. The bottom stream was then led to another whipped film evaporator at a temperature of 108° C. and a vacuum pressure of 10 mbara resulting in a bottom stream, which included 19 percent of the total inlet amount, and a distillate stream, which included 81 percent of the total inlet amount. The bottom stream included 63 weight percent 1-ethoxyethylformamide and 32.3 percent formamide. The distillate stream included 2 weight percent ethanol, 58 weight percent 1-ethoxyethylformamide, and 40 weight percent formamide.

The distillate stream withdrawn from the this distillation step was preheated to a temperature of 185° C. and pyrolyzed in a pyrolysis zone at a temperature of 400° C. in the presence of 45 grams of magnesium oxide catalyst. The feeding rate of the distillate stream to the reaction set-up was set at 45 g/hr and 175 nl/hr nitrogen was also introduced into the pyrolysis zone. The pressure of the entire system was set at 350 mbara. The resulting stream was first cooled to 60° C., whereupon a portion of the ethanol was vaporized. The resulting crude product stream included 19.7 weight percent ethanol, 33 weight percent formamide, 46.9 weight percent N-vinylformamide and 0.2 weight percent 1-ethoxyethylformamide. The total yield of N-vinylformamide was 92 percent.

The crude N-vinylformamide product stream was then subjected to a batch distillation in a column including Sulzer DX packing material with 33 theoretical plates at a vacuum pressure of 7 mbara and a top temperature of 73° C. The distillate stream had a composition of 96.4 weight percent N-vinylformamide and 2.5 weight percent formamide together with 0.1 weight percent polymerized N-vinylformamide and 1.1 weight percent of other impurities.

Definitions

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise."

As used herein, the terms "having," "has," and "have" have the same open-ended meaning as "comprising," "comprises," and "comprise."

As used herein, the terms "containing," "contains," and "contain" have the same open-ended meaning as "comprising," "comprises," and "comprise."

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

The preferred forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Equivalents to determine and assess the reasonably fair scope of the present invention as pertains to any apparatus not materially departing from but outside the literal scope of the invention as set forth in the following claims.

The invention claimed is:

1. A process for making 1-hydroxyethylformamide or N-methyl, 1-hydroxylethylformamide, said process comprising:
   (a) introducing formamide or N-methylformamide and acetaldehyde into a first reaction zone, wherein the molar ratio of formamide or N-methylformamide to acetaldehyde added to said first reaction zone is at least 1.5:1; and
   (b) reacting at least a portion of said formamide or said N-methylformamide with at least a portion of said acetaldehyde in the presence of a basic catalyst in said first reaction zone to thereby form a reaction mixture comprising 1-hydroxyethylformamide or N-methyl,1-hydroxyethylformamide
   wherein said introducing further comprises introducing at least one solvent into said first reaction zone and wherein said reacting is performed in the presence of said solvent, wherein the solubility of said 1-hydroxyethylformamide or said N-methyl,1-hydroxethylformamide in said solvent is at least 40 weight percent as determined at 20° C. using CIPAC Method MT 181.

2. The process of claim 1, wherein at least 90 weight percent of said 1-hydroxyethylformamide or said N-methyl, 1-hydroxyethylformamide formed during said reacting is maintained in solution in said reaction mixture and wherein the total solids content of said reaction mixture is not more than 10 weight percent.

3. The process of claim 1, further comprising subsequent to said reacting, combining said reaction mixture with at least one alcohol and an acid catalyst; and alkoxylating at least a portion of said 1-hydroxyethylformamide or said N-methyl,1-hydroxyethylformamide with said alcohol to thereby form another reaction mixture comprising 1-alkoxyethylformamide or N-methyl,1-alkoxyethylformamide, and wherein said reacting, said combining, and said alkoxylating are performed in sequence without an intervening solids handling step.

4. The process of claim 1, wherein said reacting is performed in a continuous reaction vessel and said reaction mixture is a single-phase liquid reaction mixture.

5. The process of claim 1, wherein said solvent is present in said first reaction zone in an amount of at least 40 weight percent, based on the total weight of said reaction mixture.

6. The process of claim 1, wherein said reaction mixture comprises not more than 10 weight percent of said solvent, based on the total weight of said reaction mixture.

7. The process of claim 1, wherein said reacting is carried out at an average reaction temperature of not more than 45° C. for a total reaction time of not more than 45 minutes and wherein said reacting is performed in a continuous plug flow reactor.

8. A process for making 1-hydroxyethylformamide or N-methyl, 1-hydroxyethylformamide, said process comprising:
(a) introducing formamide or N-methylformamide and acetaldehyde into a first reaction zone; and
(b) reacting at least a portion of said formamide or said N-methylformamide with at least a portion of said acetaldehyde in the presence of a basic catalyst in said first reaction zone to form a first reaction mixture comprising 1-hydroxyethylformamide or N-methyl,1-hydroxyethylformamide, wherein said first reaction mixture further comprises at least one solvent, wherein said 1-hydroxyethylformamide or said N-methyl,1-hydroxyethylformamide has a solubility of at least 20 weight percent in said solvent as determined at 20° C. using CIPAC Method MT 181, and wherein at least 90 weight percent of said 1-hydroxyethylformamide or said N-methyl,1-hydroxyethylformamide formed during said reacting is maintained in solution in said first reaction mixture, wherein the molar ratio of formamide to acetaldehyde or the molar ratio of N-methylformamide to acetaldehyde introduced into said first reaction zone is at least 1.1:1.

9. The process of claim 8, wherein said 1-hydroxyethylformamide or said N-methyl,1-hydroxyethylformamide has a solubility of at least 40 weight percent in said solvent as determined at 20° C. using CIPAC Method MT 181 and wherein said solvent comprises at least one $C_1$ to $C_8$ alcohol or water.

10. The process of claim 8, further comprising alkoxylating at least a portion of said 1-hydroxyethylformamide or said N-methyl,1-hydroxyethylformamide in said first reaction mixture with an alcohol in the presence of an acid catalyst in a second reaction zone to thereby form a second reaction mixture comprising 1-alkoxyethylformamide or N-methyl,1-alkoxyethylformamide, wherein said reacting and alkoxylating are performed in sequence without an intervening solids handling step.

11. The process of claim 10, wherein said reacting is carried out at a temperature of not more than 25° C. for a time of not more than 1 hour, wherein the yield of said 1-hydroxyethylformamide or said N-methyl,1-hydroxyethylformamide from said first reaction zone is at least 90 percent, wherein said alkoxylating is carried out at a temperature of at least 20° C. and not more than 45° C. and wherein the yield of said 1-alkoxyethylformamide or said N-methyl,1-alkoxyethylformamide from said second reaction zone is at least 85 percent.

12. The process of claim 8, wherein the molar ratio of formamide to 1-hydroxyethylformamide or the molar ratio of N-methylformamide to N-methyl,1-hydroxyethylformamide in said first reaction mixture is greater than 1.1:1.

13. The process of claim 8, wherein said reacting is performed in a continuous reaction vessel and wherein said first reaction mixture is a single phase reaction mixture.

14. The process of claim 1, wherein the yield of 1-hydroxyethylformamide or N-methyl,1-hydroxyethylformamide in said reaction mixture is at least 90%.

15. The process of claim 1, wherein the yield of 1-hydroxyethylformamide or N-methyl,1-hydroxyethylformamide in said reaction mixture is at least 95%.

* * * * *